(12) United States Patent
Takagi et al.

(10) Patent No.: US 6,607,917 B2
(45) Date of Patent: Aug. 19, 2003

(54) METHOD OF AND APPARATUS FOR CULTIVATING A CELL OR TISSUE

(75) Inventors: Takao Takagi, Fuji (JP); Setsuo Watanabe, Fuji (JP); Hidetada Takai, Fuji (JP); Ibuki Kinouchi, Fuji (JP); Shuichi Mizuno, Brookline, MA (US); Julie Glowacki, Jamaica Plain, MA (US)

(73) Assignees: Takagi Industrial Co., Ltd., Shizuoka-Ken (JP); The Brigham & Women's Hospital, Inc., Boston, MA (US)

( * ) Notice: Subject to any disclaimer, the term of this patent is extended or adjusted under 35 U.S.C. 154(b) by 0 days.

(21) Appl. No.: 09/895,162

(22) Filed: Jul. 2, 2001

(65) Prior Publication Data

US 2002/0037586 A1 Mar. 28, 2002

Related U.S. Application Data

(62) Division of application No. 09/796,422, filed on Mar. 2, 2001, now Pat. No. 6,432,713.

(30) Foreign Application Priority Data

Mar. 2, 2000 (JP) ......................................... 2000-057585

(51) Int. Cl.[7] .................................................. C12N 5/00
(52) U.S. Cl. ................. 435/395; 435/283.1; 435/286.6; 435/383
(58) Field of Search ................................ 435/395, 383, 435/283.1, 286.6

(56) References Cited

U.S. PATENT DOCUMENTS

| | | | |
|---|---|---|---|
| 4,452,892 A | | 6/1984 | Rosevear |
| 5,026,649 A | | 6/1991 | Lyman et al. |
| 5,162,225 A | | 11/1992 | Sager et al. |
| 5,266,476 A | * | 11/1993 | Sussman et al. |
| 5,330,915 A | | 7/1994 | Wilson et al. |
| 5,658,797 A | | 8/1997 | Bader |
| 5,686,301 A | | 11/1997 | Falfenberg et al. |
| 6,037,141 A | | 3/2000 | Banes |
| 6,048,723 A | * | 4/2000 | Banes |

FOREIGN PATENT DOCUMENTS

| | | |
|---|---|---|
| JP | 07-184634 | 7/1995 |
| JP | 7-298869 | 11/1995 |
| JP | 2000-041660 | 2/2000 |

OTHER PUBLICATIONS

International Preliminary Examination Report of the relevant PCT application No. PCT/JP01/01516.

Shuichi Mizuno et al.; "Effects of physical stimulation on chondrogenesis in vitro"; Materials Science & Engineering; 1998; vol. 6, pp 301–306.

Julie Glowacki et al. "Joint research for development of in vitro regeneration method of cartilage"; Report of the Bilateral International Joint Research by Special Coordination Funds for Promoting Science and Technology; 1997; pp. 430–435.

* cited by examiner

Primary Examiner—Leon B. Lankford, Jr.
(74) Attorney, Agent, or Firm—Connolly Bove Lodge & Hutz LLP

(57) ABSTRACT

The invention provides a method of and an apparatus for cultivating a cell or tissue capable of preventing the cell or tissue from being contaminated and realizing an efficient in vitro culture. The method of and the apparatus for cultivating a cell or tissue comprise installing a culture position (culture chamber) under an environment that is arbitrarily controlled such as an environment mimicking the living body, supplying a culture medium to the cell or tissue while the cell or tissue is held at the culture position, and cultivating the cell or tissue at the culture position that is under the ideal environment, thereby preventing the cell or tissue from being contaminated and realizing an efficient in vitro culture.

3 Claims, 27 Drawing Sheets

FIG. 10

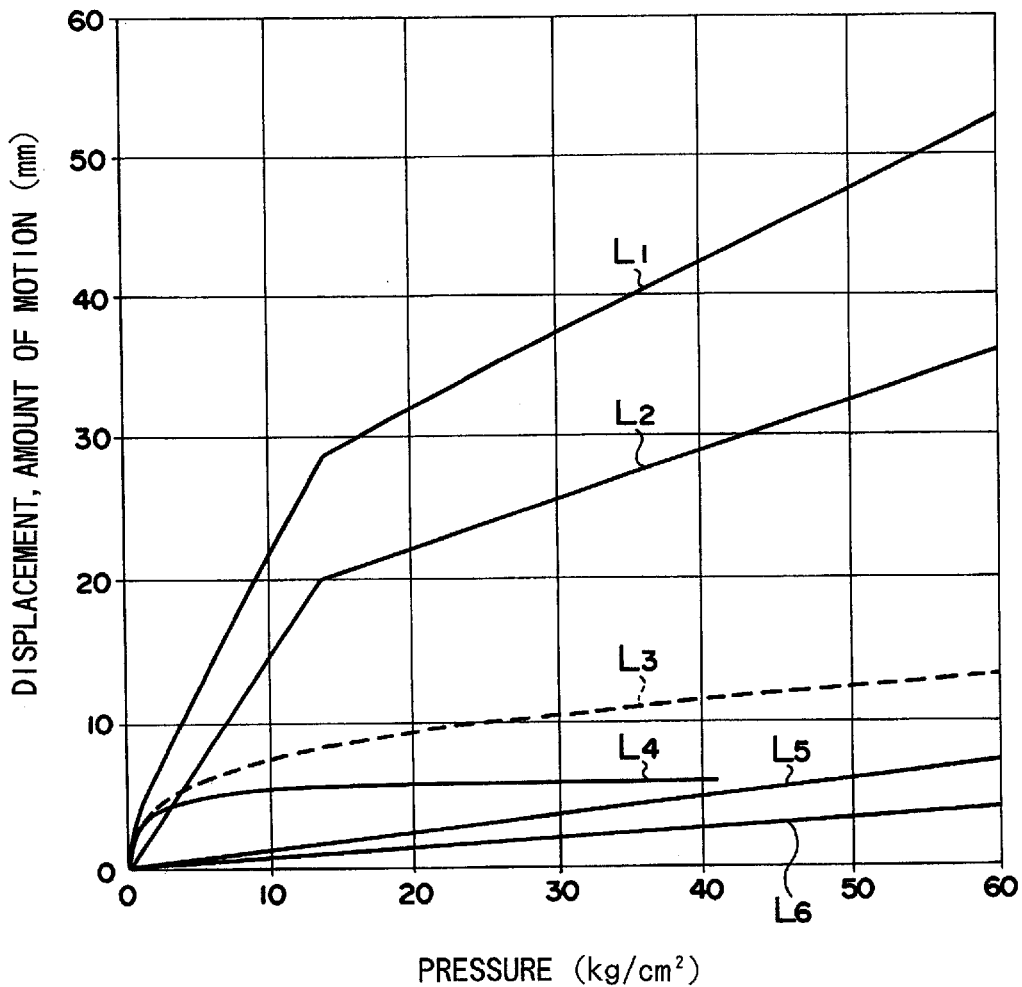

L₁ : AMOUNT OF MOTION OF MOTOR 122
L₂ : AMOUNT OF CONTRACTION OF PRESSURE APPLICATION SPRING 118
L₃ : AMOUNT OF MOTION OF PRESSURE APPLICATION PISTON 116 WHEN PRESSURE APPLICATION SPRING 118 IS NOT USED
L₄ : AMOUNT OF MOTION OF PRESSURE APPLICATION PISTON 116 OWING TO CONTRACTION OF MIXED AIR
L₅ : AMOUNT OF MOTION OF PRESSURE APPLICATION PISTON 116 OWING TO CONTRACTION OF WATER
L₆ : AMOUNT OF MOTION OF PRESSURE APPLICATION PISTON 116 OWING TO DEFORMATION OF VESSEL OF CULTURE CHAMBER 20 AND PRESSURE CHAMBER 60

$m_1$ : IN CASE OF USING A SINGLE BUFFER SPRING 154
$m_2$ : IN CASE OF USING TWO DIFFERENT SPRINGS AS THE SINGLE BUFFER SPRING 154

METHOD OF AND APPARATUS FOR CULTIVATING A CELL OR TISSUE

RELATED APPLICATIONS

The present application is a divisional of U.S. patent application Ser. No. 09/796,422, filed Mar. 2, 2001 U.S. Pat. No. 6,432,713. The present application also relates to co-pending application Ser. No. 09/895,161, being filed concurrently herewith.

BACKGROUND OF THE INVENTION

1. Field of the Invention

The invention relates to a culture technology of a cell or tissue employed by a tissue engineering that is applied to a cell or tissue engineering or genetic treatment, particularly to a method of and an apparatus for cultivating a cell or tissue (hereinafter referred to as culture method and culture apparatus) for use in an in vitro culture of a cell or tissue that is needed for restoring a damaged tissue of human body.

2. Description of the Related Art

There are following methods for restoring a damaged tissue or a pathogenic part of a living body. The first method is to substitute the damaged tissue or pathogenic part for materials other than a living body such as plastic, metal, ceramic as restoring means of the damaged tissue or the pathogenic part. As substitutable materials, there are ceramics and stainless steel for bones, a polyethylene resin for joints, and a vinyl resin for blood vessels. Second method is to substitute the damaged tissue or pathogenic part for parts of other animals or the different position of the living body. As the substitutable tissue in the second method, there are, for example, skins. The third method is to transplant of internal organs of other people.

In the first method, there is a drawback that the materials other than the living body such as plastic, metal, ceramic need to be substituted periodically by others when they are worn or consumed or materials separated from the materials other than the living body by the wear thereof affects adversely on the living body. Further, in a blood vessel made of a synthetic polymer, there is a report that an interior of the blood vessel is clogged when it is used for a long period of time. In the third method, if there is no donor for supplies his or her internal organs to be transplanted, it is impossible to carry out the third method. Even if the third method is carried out, there still remains a problem of immunological rejection between internal organs of two people.

Accordingly, a method of restoring a damaged tissue or a pathogenic part of a living body that is expected to be carried out is to substitute the damaged part of a cell or tissue by a cell or tissue that is obtained by cultivating a cell or tissue in vivo or in vitro. It is reported in current researches that there is a possibility in many tissues such as skins, cartilage, bones, blood vessels, livers, and pancreas. If a cell or tissue derived from a living body is cultivated inside or outside the living body of a patient, and the cell or tissue obtained by the culture is applied to the restoration of a damaged part, a tissue can be regenerated in the body, and further the tissue applied to the restoration would have gene of the patient per se, there does not occur immunological rejection, and further, a chemical substance such as synthetic polymer other than a living material does not adversely affect a living body, thereby realizing an ideal treatment.

There has been proposed and disclosed as a technology of this type in Japanese Patent Laid-Open Publication No. 9-313166 entitled "DEVICE FOR CULTURING CELL".

This technology needs to disassemble into each part every culture, to clean, to sterilize, and then reassemble the apparatus, resulting in a risk of contamination by bacteria after sterilization. Although each part of the apparatus can be assembled for preventing contamination by bacteria so as to perform a sterilization treatment by an autoclave (absolute pressure 2 atm. at 121° C.), this technology can not be employed in view of the contamination by bacteria because a pump and a pressure sensor include many electronic devices, a specific resin and oil. Accordingly, parts of the pump and pressure sensor are disassembled while only a passage through which a culture medium passes is taken out and is sterilized by chemicals, and other parts are sterilized by the autoclave, thereafter the pump and pressure sensor are assembled together with the apparatus, resulting in much labor and the increase of risk of contamination by various bacteria. Further, in the culture using an incubator (culture vessel), a pump or a controller is subjected to an adverse affection by a temperature or humidity, and also all the devices can not be accommodated in the incubator having a limited capacity. Accordingly, it is necessary to assemble the culture apparatus in a state where the incubator communicates with an open air for allowing piping, a power supply and a controlling electric wire to pass through a through hole of the incubator. Still further, since a pressure is applied to an entire circuit of a culture medium, the entire culture apparatus including parts of the pump and piping shall have a pressure resistant construction. As a result, it is very difficult to place the apparatus at high pressure e.g. not less than 1 MPa, and even if a high pressure is applied to the apparatus, the apparatus shall be high pressure resistant as a whole, resulting in a problem of high cost.

More still further, there is a research reported by Dr. Shuichi MIZUNO et al. in Harvard Medical School that a tissue of a living body is cultivated by applying a pressure to the living body as physical stimulation (see Materials Science and Engineering C6 (1998) 301-306). According to this research, a culture apparatus is formed as illustrated in FIG. 26. Each constituent and function thereof in this culture apparatus is described now.

A pump 400 has a role to circulate a culture medium 402 therein and to pressurize the interior of a culture chamber 404 to supply a hydraulic pressure to a cell 406 or tissue, and it is formed of a pump for use in a liquid chromatograph, and further it has a control unit built therein for flowing a given amount of fluid.

A back pressure regulator 408 allows a pressure to escape through a valve 410 by opening the valve 410 when a pressure exceeds a pressure to be applied to the cell 406 or tissue exceeds so as to hold the pressure inside the culture chamber 404 constant. The back pressure regulator 408 is selectively provided in a circuit 426, described later, depending on a pressure to be applied to the cell 406.

The culture chamber 404 forms a space for cultivating the cell 406 or tissue, and a scaffold 412 formed of a sponge made of a collagen in which the cell 406 or tissue is transplanted is accommodated in the space. The cell 406 or tissue grows on the scaffold 412 formed of a sponge made of a collagen. A pressure sensor 414 detects a pressure inside the culture chamber 404 while a pressure monitor 416 indicates the pressure detected by the pressure sensor 414. The pump 400 is controlled by the pressure detected by the pressure sensor 414 and it stops its operation when the detected pressure increases to a large extent.

A culture medium tank 418 stores therein the culture medium 402 adapted for the cell 406 or tissue to be cultivated and the culture medium 402 comprises e.g., amino acids, saccharides, salts, and so forth. The culture medium tank 418 communicates with an open air through a vent tube 422 that penetrates a closed stopper 420, and a vent filter 424 prevents the culture medium 402 from being contaminated by an open air.

The culture apparatus is accommodated in an incubator forming a hermetically sealed space. The incubator is a space for forming a pleasant cultivating atmosphere and it is maintained under the optimum temperature, humidity and gas concentration (oxygen and carbon dioxide) that is optimized for the cell or tissue. The culture medium 402 is filled in the circuit 426 by the pump 400 and circulated therein. The oxygen and carbon dioxide are soluble in the culture medium 402 after they pass through the vent filter 424, and the culture medium 402 is kept under appropriate oxygen concentration and carbon dioxide concentration. When the pump 400 is operated, a pressure inside the culture chamber 404 gradually increases. When the pressure exceeds a given value set by the back pressure regulator 408, the valve 410 of the back pressure regulator 408 is opened to discharge the culture medium 402 so that a pressure of the culture medium 402 is decreased by the amount of the discharged culture medium 402, thereby shutting the valve 410. With the repetition of these operations, a fixed pressure is maintained, and at the same time a fixed amount of the culture medium 402 is repetitively circulated. The cell 406 or tissue grows while it is subjected to such pressure application stimulation.

Although a fixed pressure is maintained in this culture apparatus, the increase and decrease of a pressure can not be repeated. Since the increase of the pressure is made by the pump 400, the rate of increase of the pressure is determined by the capacity of the pump 400. If the amount of circulation of the culture medium 402 increases, the rate of increase of the pressure becomes fast, while if the amount of circulation of the culture medium 402 decreases, the rate of increase of the pressure becomes slow. Accordingly, if a pressure cycle is continuously repeated, there is a method of providing a bypass 432 having a bypass valve 428 and an orifice valve (needle valve) 430 in parallel with a back pressure regulator 408 as shown in FIG. 27 to decrease the pressure. In this method, although the pressure can be decreased, there is a drawback that it takes a long time for one cycle, and the setting of a repetitive cycle and the circulation amount of the culture medium 402 can not be independent from each other, and further the regulation of the orifice valve 430 is finely controlled so as to render the rate of decrease of the pressure unstable.

Since the culture apparatus has to be assembled after each component thereof is disassembled, cleaned and sterilized every performance of culture, there is the risk of contamination by the bacteria after sterilization. Although it is possible to subject the assembled culture apparatus to a sterilization treatment by an autoclave (absolute pressure 2 atm. at 121° C.), the pump and pressure sensor can not be sterilized because they include many electronic devices, specific resin and oil. Accordingly, under the existing circumstances, only a passage through which the culture medium 402 passes is taken out while each part of the pump and pressure sensor is disassembled, and each part is subjected to a sterilization by chemicals. The other parts of the pump and pressure sensor are subjected to a sterilization by an autoclave, then the pump, pressure sensor and the culture apparatus are respectively assembled, resulting in much labor and a risk of contamination by various bacteria.

Although oxygen and carbon dioxide are taken in the culture medium 402 through a filter, they are directly taken in from an ambient atmosphere, resulting in a risk of the contamination by bacteria. Further, although the culture apparatus is accommodated in an incubator, a pump unit and a pressure monitor is susceptible to a temperature and humidity so that the pump unit and pressure monitor are hardly accommodated in the incubator in view of their capacities. Accordingly, it is necessary to assemble the culture apparatus by allowing a tube for piping, a power supply and an electric wire for controlling to pass through a through hole of the incubator so that the inside and outside thereof are connected to each other.

Since a pressure is set by selecting a back pressure regulator depending on a set pressure, when the setting of a pressure is changed, the back pressure regulator is replaced by another one, resulting in much labor and a risk of contamination by various bacteria.

When a pressure cycle is changed, a pressure at a low pressure side can not be set in the culture apparatus in FIG. 27, but the pressure can be regulated by the orifice valve 430 so that the set pressure is varied by the quantity of circulated flow through the pump 400 even if a pressure can be regulated to some extent by the orifice valve 430.

As set forth above, in the conventional method of cultivating a cell or tissue of a living body, the cell is cultivated under a condition where a temperature, a humidity, a concentration of carbon dioxide and a concentration of oxygen are optimally set in an incubator. In such a culture in the incubator, it is a two-dimensional culture on a laboratory dish, and a three-dimensional culture has been now tried. Further, in such a culture method, a culture medium, cell or tissue that is exposed by an open air is prone to contamination by bacteria, so that stable culture is hardly performed.

Further, since the cell of a living body is always placed under physical stimulation and the stimulation indirectly affects the control of metabolism of a cell, a cell division cycle, a concentration gradient and dispersion of living body stimulation, and hence stable culture is hardly realized, and further, it has been hard to set or change the amount, variation, cycle of the physical stimulation. More still further, delicate set and regulation of a pressure are needed in culture, which requires a skill of a person in charge of culture.

Accordingly, in the conventional in vitro culture of a living cell, it takes time for a cell to grow to the same size as a cell to be restored, and hence there occurs a case where a normal culture is marred by contamination.

SUMMARY OF THE INVENTION

It is therefore an object of the invention to provide a method of and an apparatus for cultivating a cell or tissue capable of preventing the cell or tissue from being contaminated, and of realizing an efficient in vitro culture.

According to the invention, a culture position (culture chamber) is installed under an arbitrarily controlled environment such as an environment mimicking the living body, a culture medium is supplied while a cell or tissue is held in the foregoing culture position so that the cell or tissue is cultivated at the culture position under an ideal environment, whereby the cell or tissue is prevented from contamination and an efficient in vitro culture thereof can be realized.

To achieve the above object, the method of cultivating a cell or tissue according to the first aspect of the invention is characterized in comprising holding a cell or tissue of a living body at a specific culture position, setting the cell or tissue under an environment mimicking the living body, supplying a culture medium to the cell or tissue, and cultivating the cell or tissue at the culture position.

That is, it is ideal that a tissue necessary for restoring a damaged tissue of a living body and so forth is used by a cell or tissue of the same living body. It is necessary to cultivate or to perform an in vitro culture using a cell or tissue collected from the living body to realize it. It is important for the in vitro culture that the contamination is prevented and a culture environment likewise a living body, namely, an environment mimicking the living body is artificially realized. For this end, a culture position is set under an environment formed artificially and the cell or tissue is held at a culture position and the culture medium is supplied to realize the in vitro culture of the cell or tissue. An environment means living condition including internal or external stimulation needed for maintaining a life healthy on the basis of a living body formed of a cell or tissue. The culture medium includes a nutrition source needed for maintaining the life of a cell or tissue and growing it. In this case, the supply of the culture medium applies a hydraulic pressure and physical stimulation to the cell or tissue, so that the cell or tissue is susceptible to metabolism functions, cell division cycle, concentration gradient or dispersion of living body stimulation so that the culture is enhanced. As a result, it is possible to cultivate the cell or tissue which is close to a tissue in a living body and easily fusible with a tissue in a living body.

The method of cultivating a cell or tissue according to the second aspect of the invention is characterized in comprising holding a cell or tissue of a living body at a specific culture position (culture chamber), setting the cell or tissue under an environment mimicking the living body, supplying continuously or intermittently a culture medium to the cell or tissue by way of a culture circuit (culture circuit), applying a pressure which is varied continuously, a pressure which is varied intermittently or a pressure which is varied periodically to the cell or tissue, and cultivating the cell or tissue at the culture position.

The setting of the culture position and environment are the same as mentioned above. The culture medium is continuously or intermittently supplied to the cell or tissue that is set at the culture position through the culture circuit. When the culture medium is supplied to the cell or tissue through the culture circuit that is separated or intercepted from the outside, the mode of supply of the culture medium can be made continuous or intermittent, and also the prevention of contamination can be achieved. It is possible to mimic a living body and to cultivate the cell or tissue efficiently by controlling the mode of the supply of the culture medium, corresponding to a living body environment. A desired pressure acts on the cell or tissue under culture thereof to apply physical stimulation. The mode of application of pressure is varied continuously, intermittently or periodically to mimic a living body, and apply a physical or mechanical strength needed for a living body such as flexibility or durability needed for the cell or tissue to be cultivated. Accordingly, it is possible to contribute to the culture of a cell or tissue which is ideal or practical, corresponding to a living body at a specific position of a living body, namely, contribute to cultivate the cell or tissue which is close to a tissue in a living body and easily fusible with a tissue in a living body.

The method of cultivating a cell or tissue according to the third aspect of the invention is characterized in further providing holding means for holding the cell or tissue to be cultivated at the culture position in a suspending or non-suspending state in the culture medium. That is, an experiment confirmed that the cell or tissue to be cultivated is held in a static state, that is needed for enhancing a culture efficiency.

The method of cultivating a cell or tissue according to the fourth aspect of the invention is characterized in that the holding means employs a hydro-gel for holding the cell or tissue to be cultivated at the culture position in a suspending state in the culture medium or a scaffold for holding the cell or tissue and absorbing the cell or tissue when it grows. That is, the cell or tissue to be cultivated may be held in any way, and hydro-gel or scaffold is one example of holding the cell or tissue in this case. The hydro-gel is means for wrapping and holding the cell or tissue to be cultivated in a suspending state, and the cell or tissue can be taken out from the hydro-gel when the culture is completed. Further, the scaffold may comprise a porous body formed of protein, and the cell or tissue to be cultivated is held by the scaffold and absorbs the scaffold as a nutrition as it grows.

The method of cultivating a cell or tissue according to the fifth aspect of the invention is characterized in that the culture medium includes one or not less than two of amino acids of various types, saccharides, salts and protein. That is, it is possible to use the culture medium corresponding to the cell or tissue to be cultivated, for example, it is possible to use one of amino acids of various types, saccharides, salts and protein or not less than two of materials selected therefrom or all of these materials. The selection of the culture medium is an essential element for efficient culture or for forming the cell or tissue with high quality.

The method of cultivating a cell or tissue according to the sixth aspect of the invention is characterized in that the environment mimicking the living body under which the cell or tissue is cultivated is set depending on physiological conditions of the living body at a specific position, an age, a height, a weight, a sex of the living body and other information inherent in the living body in addition to the physiological conditions of the living body. That is, it is very important that the cell or tissue for use in restoring a part of a living body conformed to the living body, and the culture environment can be set by use of information inherent to the living body serving as one element.

The method of cultivating a cell or tissue according to the seventh aspect of the invention is characterized in that the environment mimicking the living body under which the cell or tissue is cultivated is set by a nitrogen gas, an oxygen gas, a carbon dioxide gas respectively supplied through the culture medium, a temperature and a humidity. That is, since it is desirable that an environment under which the cell or tissue is cultivated corresponds to a living body, for example, if nitrogen gas, oxygen gas or carbon dioxide gas is supplied to a cultivation space and a temperature or humidity is set to that adapted for cultivation, a living body environment can be controlled to a desired state.

The method of cultivating a cell or tissue according to the eighth aspect of the invention is characterized in that the pressure applied to the cell or tissue can be arbitrarily set depending on the specific position of the living body. That is, it is possible to form an ideal or practical cell or tissue by applying a pressure, corresponding to the a living body at a specific position to be restored.

The method of cultivating a cell or tissue according to the ninth aspect of the invention is characterized in that the pressure applied to the cell or tissue is a pressure which is varied continuously, a pressure which is varied intermittently or a pressure which is varied periodically or a pressure combining these pressures. That is, it is possible to form the pressure pattern that is varied continuously, intermittently or periodically, and it is selected or combined to realize ideal physical stimulation so as to affect metabolism function, cell division cycle, concentration gradient or dispersion of living body stimulation so that the culture is enhanced.

The apparatus for cultivating a cell or tissue according to the tenth aspect of the invention is characterized in comprising a culture unit (culture circuit unit) having a culture chamber containing therein a cell or tissue and supplying culture medium, pressure application means (pressure application apparatus) for applying a pressure to the cell or tissue in the culture chamber, and culture medium supply means (culture medium supply apparatus) for intermittently or continuously supplying the culture medium to the culture unit.

That is, the culture unit accommodates the cell or tissue to be cultivated in the culture chamber to supply a culture medium needed for the cell or tissue that is intercepted from the open air. The cell or tissue that is intercepted from the open air is protected from contamination by bacteria and so forth, and hence it grows to a tissue having an excellent quality. A desired pressure by pressure application means in addition to physical stimulation caused by a hydraulic pressure and a flow by the culture medium is applied to the cell or tissue. As a result, it affects metabolism function, cell division cycle, concentration gradient or dispersion of living body stimulation so that the culture is enhanced. The mode of supply of the culture medium to the cell or tissue is arbitrarily set by the culture medium supply means, and the culture medium can be supplied to the cell or tissue intermittently or continuously so that the culture is enhanced by a variety of physical stimulation. The mode of the supply of the culture medium includes one of or both of the supply of a new culture medium at all times or the supply of the culture medium by repetitively circulating the culture medium. In the mode of circulation of the culture medium can save the culture medium, but there is an advantage of the prevention of the variation in concentration of the culture medium when supplying the culture medium in one direction.

The apparatus for cultivating a cell or tissue according to the eleventh aspect of the invention is characterized in further providing control means for controlling the pressure application means or culture medium supply means. That is, although the pressure application means or culture medium supply means can be controlled arbitrarily, various controls such as a feed back control or feed forward control and a program control and so forth can be performed by use of control means such as a computer. It is needless to say to add a personal collection control by an interruption, and the collection control is not excluded.

The apparatus for cultivating a cell or tissue according to the twelfth aspect of the invention is characterized in that the pressure applied from the pressure application means to the cell or tissue can be arbitrarily set depending on the cell or tissue. The manner of applying a pressure, namely, a pressure pattern is set, corresponding to a cell or tissue to be cultivated, thereby performing an efficient culture.

The apparatus for cultivating a cell or tissue according to the thirteenth aspect of the invention is characterized in that the pressure applied from the pressure application means to the cell or tissue is a pressure which is varied intermittently, a pressure which is repeated every given time or a pressure which increases or decreases every given time. That is, the pressure pattern can be conceived in all modes, thereby cultivating cell or tissue efficiently by selecting a mode of pressure pattern.

The apparatus for cultivating a cell or tissue according to the fourteenth aspect of the invention is characterized in that the culture unit is independent of and detached from a culture apparatus body. That is, the culture unit having the culture chamber for accommodating therein the cultivated cell or tissue can be independent of and detached from a culture apparatus body so that the cell or tissue can be moved together with the culture unit that is separated from the open air to protect the cell or tissue from being contaminated by bacteria during the motion thereof.

The apparatus for cultivating a cell or tissue according to the fifteenth aspect of the invention is characterized in that the culture unit is accommodated in a hermetically sealed space that is intercepted from an open air. That is, since the hermetically sealed space is the culture space, and it is intercepted from an open air, it is possible to set a culture environment by the supply of the desired gas, to protect the cell or tissue from the contamination by the open air.

The apparatus for cultivating a cell or tissue according to the sixteenth aspect of the invention is characterized in that the culture apparatus further comprises gas absorption means capable of absorbing a nitrogen gas, an oxygen gas, a carbon dioxide gas. That is, a nitrogen gas, an oxygen gas, a carbon dioxide gas can be supplied to the culture unit accommodated in the hermetically sealed space and the gas absorption means is provided in the culture unit so that the gas is applied to the cell or tissue and a living environment can be mimicked by supplying and controlling gas.

The apparatus for cultivating a cell or tissue according to the seventeenth aspect of the invention is characterized in that the hermetically sealed space is filled with a nitrogen gas, an oxygen gas, a carbon dioxide gas. That is, when a nitrogen gas, an oxygen gas, a carbon dioxide gas is filled in the culture space formed by the hermetically sealed space, a living body environment can be mimicked.

The apparatus for cultivating a cell or tissue according to the eighteenth aspect of the invention is characterized in further comprising a culture medium tank for storing therein the culture medium to be supplied to the culture unit. That is, the culture medium supply source is needed for supplying or circulating a necessary culture medium to the culture unit, and the culture medium tank is a supply source. Particularly, it is possible to prevent the culture medium held in the culture unit from being contaminated, if the culture medium tank is installed in the hermetically sealed space that is intercepted from the open air.

The apparatus for cultivating a cell or tissue according to the nineteenth aspect of the invention is characterized in that the culture chamber includes a pressure transmitting film for receiving a pressure from the outside. That is, it is possible to apply pressure application stimulation to the cell or tissue accommodated in the culture chamber in a state wherein it is intercepted from an open air, and to realize desired pressure application stimulation such as stimulation mimicking a living body environment by providing the pressure transmitting film.

The apparatus for cultivating a cell or tissue according to the twentieth aspect of the invention is characterized in that the culture chamber includes pressure buffering means. That is, it is possible to realize physical stimulation close to a living body environment and to enhance the culture of the cell or tissue by regulating a pressure by pressure buffering means when a part of a culture unit is pressurized.

The apparatus for cultivating a cell or tissue according to the twenty-first aspect of the invention is characterized in that the apparatus in the tenth aspect of the invention further comprises a pressure chamber fixed to the culture chamber by way of a pressure transmitting film, and a pressure is applied to the cell or tissue in the culture chamber by allowing a hydraulic pressure, an oil pressure or an air pressure to act on the cell or tissue in the culture chamber. That is, it is possible to realize desired pressure application stimulation and to mimic a living body environment with high accuracy by using any of the hydraulic pressure, the oil pressure or the air pressure as pressure forming means.

The apparatus for cultivating a cell or tissue according to the twenty-second aspect of the invention is characterized in that the culture medium supply means comprises a medium supply chamber provided in the culture unit and a medium supply unit for pressuring a culture medium that is taken in the medium supply chamber and supplying the pressurized culture medium. That is, the culture medium supply means is means for supplying and circulating the culture medium in the culture unit, and it is formed of various types, for example, if it is formed of the medium chamber and the medium supply unit for pressuring a culture medium that is taken in the medium supply chamber, the amount of applied pressure can be controlled to set a desired amount of supply medium.

The apparatus for cultivating a cell or tissue according to the twenty-third aspect of the invention is characterized in that a relief valve is provided in the culture, and when a pressure of the culture medium exceeds a given pressure which is arbitrarily set to the relief valve, the relief valve is opened to decrease the pressure of the culture medium. That is, it is important to buffer the pressure to be applied to the culture for applying ideal pressure application stimulation to the cell or tissue. If the pressure relieve valve is used as one means, and it is opened to decrease the pressure of the culture medium when the pressure of the culture medium exceeds a given pressure which is arbitrarily set to the relief valve, the culture medium is controlled in an ideal pressure state without contaminating the culture medium.

The apparatus for cultivating a cell or tissue according to the twenty-fourth aspect of the invention is characterized in that heating means or humidifying means are provided in a hermetically sealed space and the hermetically sealed space is kept and controlled at a desired temperature or humidity. That is, it is possible to provide a culture space conforming to a living body environment by controlling a temperature and a humidity of the hermetically sealed space in which the culture unit is accommodated.

The apparatus for cultivating a cell or tissue according to the twenty-fifth aspect of the invention is characterized in that a sound producing unit for applying a super-sound wave or the like sound wave in the culture chamber in the culture unit. That is, it is possible to mimic a living body environment acoustically by using the sound producing unit together because a living body receives acoustic stimulation from the outside, and possible to inject the cell or tissue to be cultivated in a culture chamber by use of a super-sound wave together with high reliability.

The apparatus for cultivating a cell or tissue according to the twenty-sixth aspect of the invention is characterized in that the apparatus further comprises control means for controlling concentration of a gas to be supplied to the hermetically sealed space. That is, it is possible to mimic a living body environment to enhance the culture of the cell or tissue by controlling the concentration of a gas to be supplied to the hermetically sealed space by controlling means.

The objects, features and advantages of the invention are now made more clear with reference to the following first to fourth embodiments of the invention, detail descriptions thereof and the attached drawings.

BRIEF DESCRIPTION OF THE DRAWINGS

FIG. 10 is a view showing a displacement of a pressure application piston in the pressure application apparatus and a pressure chamber relative to the motion of the pressure application piston;

DETAILED DESCRIPTION OF THE PREFERRED EMBODIMENTS

First Embodiment (FIGS. 1 to 13)

A method of and apparatus for cultivating a cell or tissue according to a first embodiment of the invention is described with reference to FIGS. 1 to 13.

Figure 1:
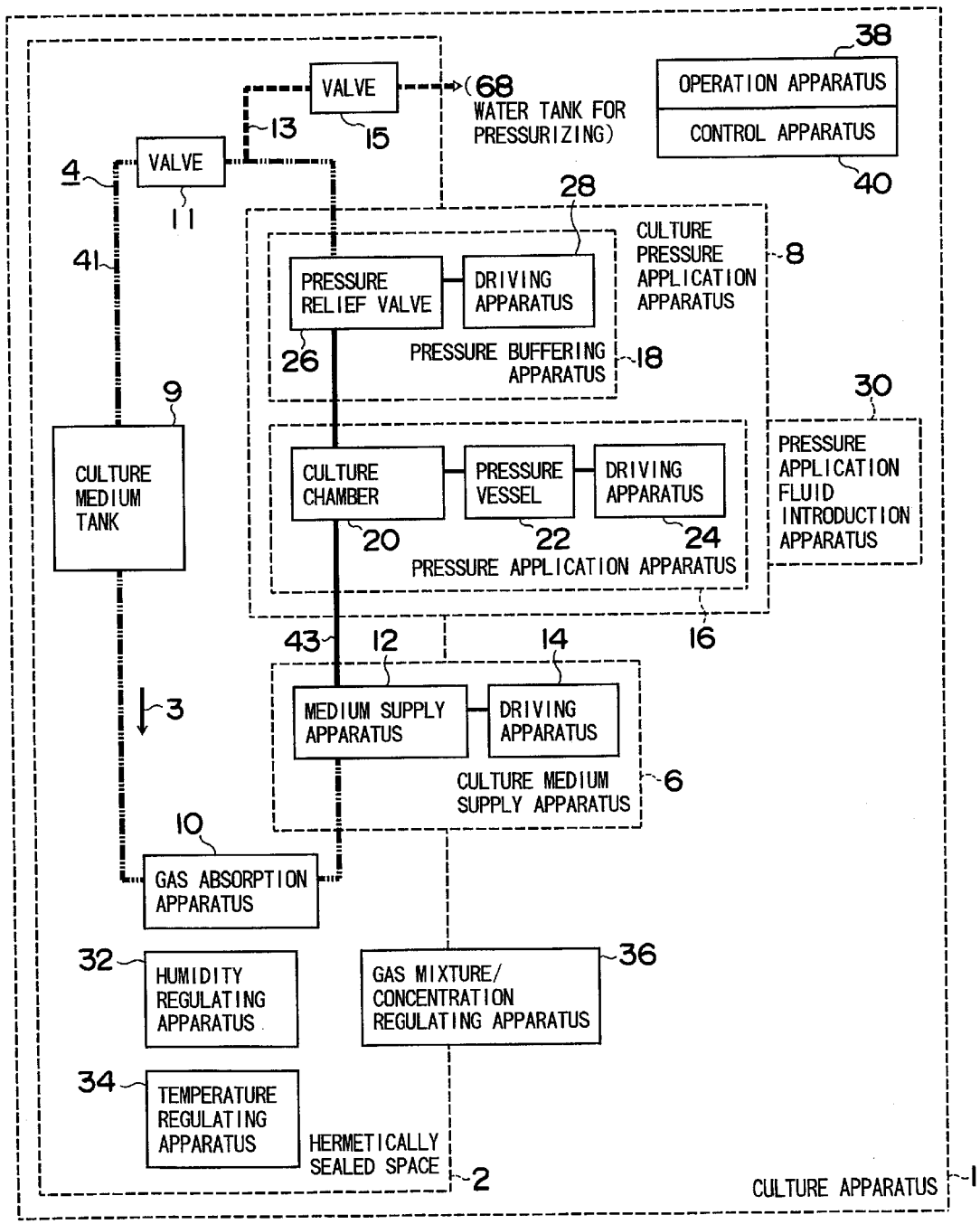
FIG. 1 is a block diagram showing a method of and an apparatus for cultivating a cell or tissue according to a first embodiment of the invention.

FIG. 1 is a block diagram showing the method of and th apparatus for cultivating a cell or tissue according to the first embodiment of the invention;

A culture apparatus 1 for realizing the method of cultivating a cell or tissue has a hermetically sealed space 2 as a culture space in which a culture circuit unit 4 serving as a culture unit to supply culture medium 3 to cell or tissue to be cultivated is installed.

The culture circuit unit 4 can be set up so as to be separated or detachable from a body of the culture apparatus 1 (hereinafter referred to as culture apparatus body). The culture circuit unit 4 includes a culture medium tank 9, culture medium supply apparatus 6, a culture pressure application apparatus 8, a gas absorption apparatus 10, a valve 11, and a branched path 13 having a valve 15 thereon. The culture medium 3 is a carrier for supplying a nutrition to the cell or tissue to be cultivated and a fluid including essential amino acid and various amino acids, glucose (saccharide), and an sometimes inorganic material such as $Na^+$, $Ca^{++}$ is added thereto depending on the cell or tissue to be cultivated or a protein such as serum is included therein. Further, these apparatus are formed of a resin material having a sufficient heat resistance and does not melt to produce a material that affects a living body such as a fluorine resin, PEEK, a high grade heat resistant polypropylene, silicone or stainless steel, thereby preventing the constituents from being contaminated.

The valves 11, 15 may be formed of a pinch valve and so forth. The culture circuit unit 4 forms a closed loop circuit when the valve 15 is shut and the valve 11 is opened, an entire open loop circuit when the valve 15 is opened and the valve 11 is shut, and a partial open loop circuit when both the valves 11, 15 are opened. The culture circuit unit 4 may includes a gas absorption portion 41 denoted by two dotted one chain line and a pressure resistant portion 43 denoted by a solid line instead of the gas absorption apparatus 10 that is partially installed therein. The gas absorption portion 41 is a portion to render gas filled in the hermetically sealed space 2 to be absorbed by the culture medium 3 while the pressure resistant portion 43 is a portion to assure a reliable medium supply, corresponding to the pressure application portion of the culture medium 3 so as to prevent leakage of medium. A tube formed of an elastomer material through which gas easily passes a gas such as $Co_2$, $O_2$ may be used in the gas absorption portion 41.

The culture medium tank 9 is accommodated in the hermetically sealed space 2 and means for storing therein the culture medium 3 that is needed for cultivating the cell or tissue. The culture medium supply apparatus 6 is means for supplying the culture medium 3 to the culture circuit unit 4, namely, when a medium supply apparatus 12 that is inserted into the culture circuit unit 4 is driven by a driving apparatus 14, it supplies a predetermined amount of culture medium 3 to the culture circuit unit 4. The culture pressure application apparatus 8 is means for applying a pressure to a cell 5 (FIG. 3) or tissue to be cultivated, and includes a pressure application apparatus 16 and a pressure buffering apparatus 18. The pressure application apparatus 16 comprises a culture chamber 20 of the culture circuit unit 4, a pressure vessel 22 attached to the culture chamber 20 and a driving apparatus 24 for allowing an arbitrary pressure to act on the culture chamber 20. A cell or tissue to be cultivated is transplanted in a scaffold formed of a collagen and so forth and it is accommodated in the culture chamber 20 and is separated from the outside.

The pressure buffering apparatus 18 is means for buffering a pressure to be applied to the culture medium 3 by the culture pressure application apparatus 8, and it sets a pressure of the culture medium 3 exceeding a predetermined value as the maximum pressure by driving a pressure relief valve 26 that is inserted into the culture circuit unit 4 by a driving apparatus 28. When a pressure of the culture medium 3 exceeding the maximum pressure acts on the culture circuit unit 4, the pressure buffering apparatus pressure 18 operates the pressure relief valve 26 to allow the culture medium 3 to escape therefrom, thereby buffering the pressure. A pressure application fluid is introduced into the pressure vessel 22 from a pressure application fluid introduction apparatus 30 provided together with the culture pressure application apparatus 8.

A humidity regulating apparatus 32, a temperature regulating apparatus 34, and a gas mixture/concentration regulating apparatus 36 are installed in the culture apparatus 1 to regulate an atmospheric humidity, an atmospheric temperature and gas mixture and concentration. An operation apparatus 38 and a control apparatus 40 are respectively installed in the culture apparatus 1, wherein desired control operations are performed by an administrator using the operation apparatus 38 while the control apparatus 40-is means for controlling a various apparatus such as the culture medium supply apparatus 6, culture pressure application apparatus 8, pressure application fluid introduction apparatus 30, humidity regulating apparatus 32, temperature regulating apparatus 34, gas mixture/concentration regulating apparatus 36 in response to an operation input or a control program through the operation apparatus 38.

The method of cultivating the cell or tissue using the culture apparatus is described next. Indispensable items such as culture conditions are inputted to the control apparatus 40 by operating the operation apparatus 38 for preparing culture.

In this case, the indispensable items are various pressures set in the culture medium 3, and they are set to a mode of, for example, a maximum pressure, a minimum pressure, a pressure gradient such as increase or decrease of pressure, a pressure application period, the amount of flow of the culture medium 3, a culture temperature and culture time. The culture circuit unit 4 selectively switches between the valves 11, 15 to render them to open or shut so as to form a closed loop or an open loop.

Then a scaffold 7 (FIG. 3) formed of a sponge such as collagen is provided in the culture chamber 20 and the cell 5 (FIG. 3) or tissue to be cultivated is transplanted in the scaffold 7. The sponge such as collagen may be formed by freezing or drying collagen fluid inside the culture chamber 20.

Subsequently, a prescribed amount of culture medium 3 is introduced into the culture medium tank 9, and the hermetically sealed space 2 is closed, then the operation switch is turned on so as to prepare the culture operation (automatic operation) so that a pressure application fluid is supplied from the pressure application fluid introduction apparatus 30 to the pressure vessel 22 side.

When the culture medium supply apparatus 6 is driven, the culture medium 3 flows to the culture chamber 20 side through the medium supply apparatus 12 so that the culture medium 3 is supplied to the cell or tissue to be cultivated. The mode of supplying the culture medium 3 is selected from a continuous supply, an intermittent supply, a periodic supply or the combination thereof.

The cell or tissue held by the scaffold is accommodated in the culture chamber 20 filled with the culture medium 3 and a pressure is applied from the pressure vessel 22 to the cell or tissue. The mode of pressure depends on pressure patterns set during the preparation of culture.

When a pressure applied to the culture medium 3 exceeds a set pressure, the culture medium 3 flows out from the pressure resistant portion 43 through the pressure relief valve 26 so that a pressure is controlled.

If such operations are repeated during a prescribed culture time, the cell or tissue grows until it reaches a desired size inside the culture chamber 20. If a sponge such as collagen is used as a scaffold, the cell or tissue to be cultivated absorbs the collagen so that the scaffold disappears naturally.

If a hydro-gel is used as holding means, the cell or tissue is accommodated and held inside the hydro-gel in a suspending state.

If the culture circuit unit 4 forms the closed loop when the valve 15 is shut and the valve 11 is opened, the culture medium 3 circulates inside the culture circuit unit 4 and it is supplied to the cell or tissue side to be cultivated. If the culture circuit unit 4 forms the opened loop when the valve 11 is shut and the valve 15 is opened, the culture medium 3 flows to the branched path 13 side then to the pressure application fluid introduction apparatus railroad ties 30 side, namely, to a water tank for pressurizing 68 side (FIG. 2) so that fresh culture medium 3 can be always supplied to the cell or tissue side to be cultivated.

A gas such as nitrogen, oxygen, carbon dioxide is absorbed by the gas absorption apparatus 10 or gas absorption portion 41 of the culture circuit unit 4 from the interior of the hermetically sealed space 2 during the culture and supplied to the culture medium 3 so that a gas that is needed for gas exchange like a living body is supplied to the cell or tissue through the culture medium 3.

In such a manner, a culture environment mimicking the living body is set in the cell or tissue so that an in vitro culture can be efficiently performed while it is not contaminated by bacteria and so forth. That is, since a hydraulic pressure of the culture medium 3 and physical stimulation by the flow of the culture medium 3 are applied to the cell or tissue inside the culture chamber 20, the cell or tissue is susceptible to metabolism function, cell division cycle, concentration gradient or dispersion of living body stimulation so that the culture is enhanced. Further, the cell or tissue is subjected to physical stimulation by a pressure application by the pressure application apparatus 16 or depending on the mode of pressure application. Accordingly, the culture of the cell or tissue is enhanced so that a tissue close to that in the living body or a tissue easily fuses with the tissue of the living body can be cultivated. Still furthr, if the pressure resistant portion 43 is partially provided, a cost needed for the pressure resistant construction can be reduced.

Figure 2:
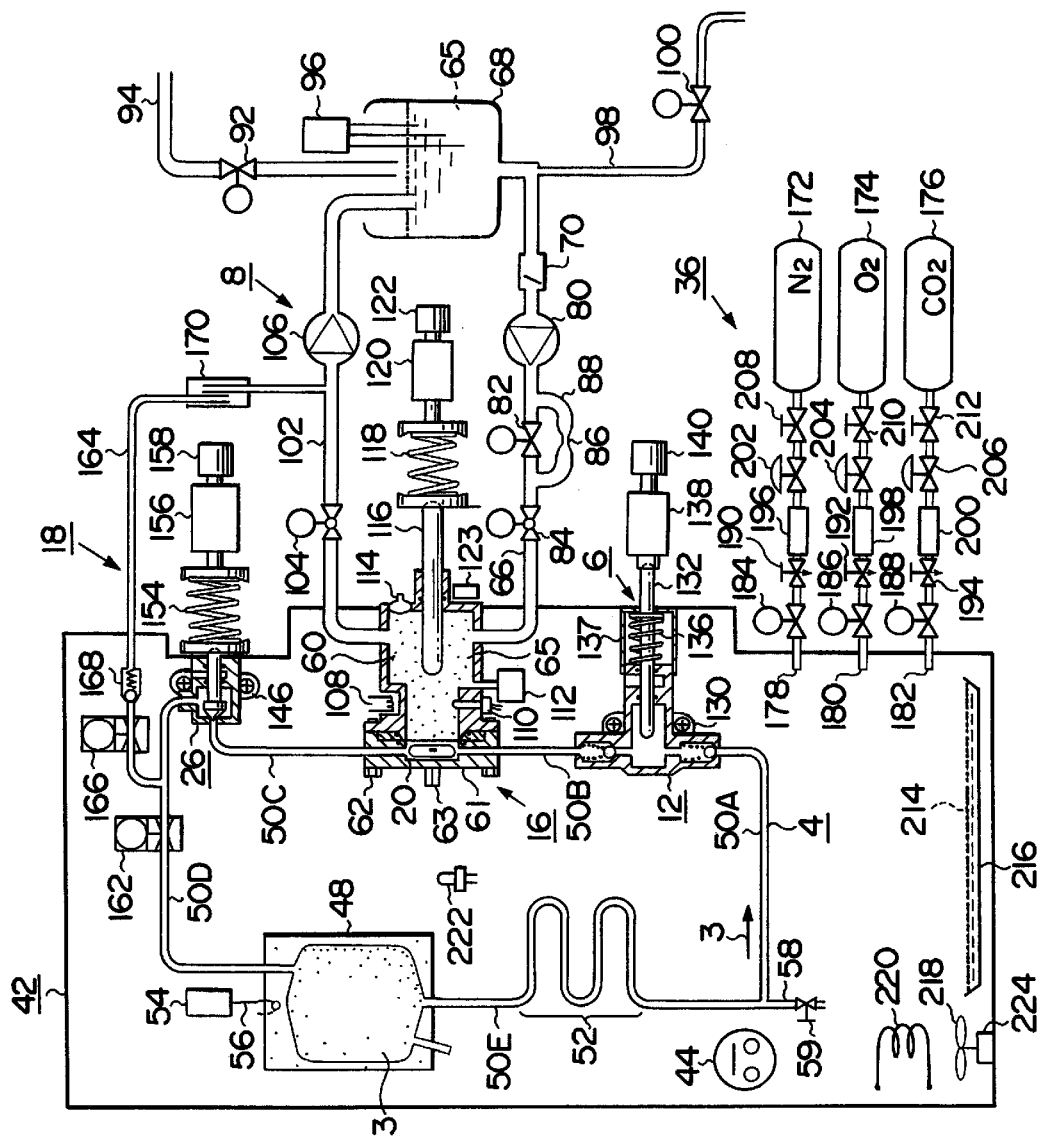
FIG. 2 is a view showing the method of and the apparatus for cultivating a cell or tissue in FIG. 1.
Figure 3:
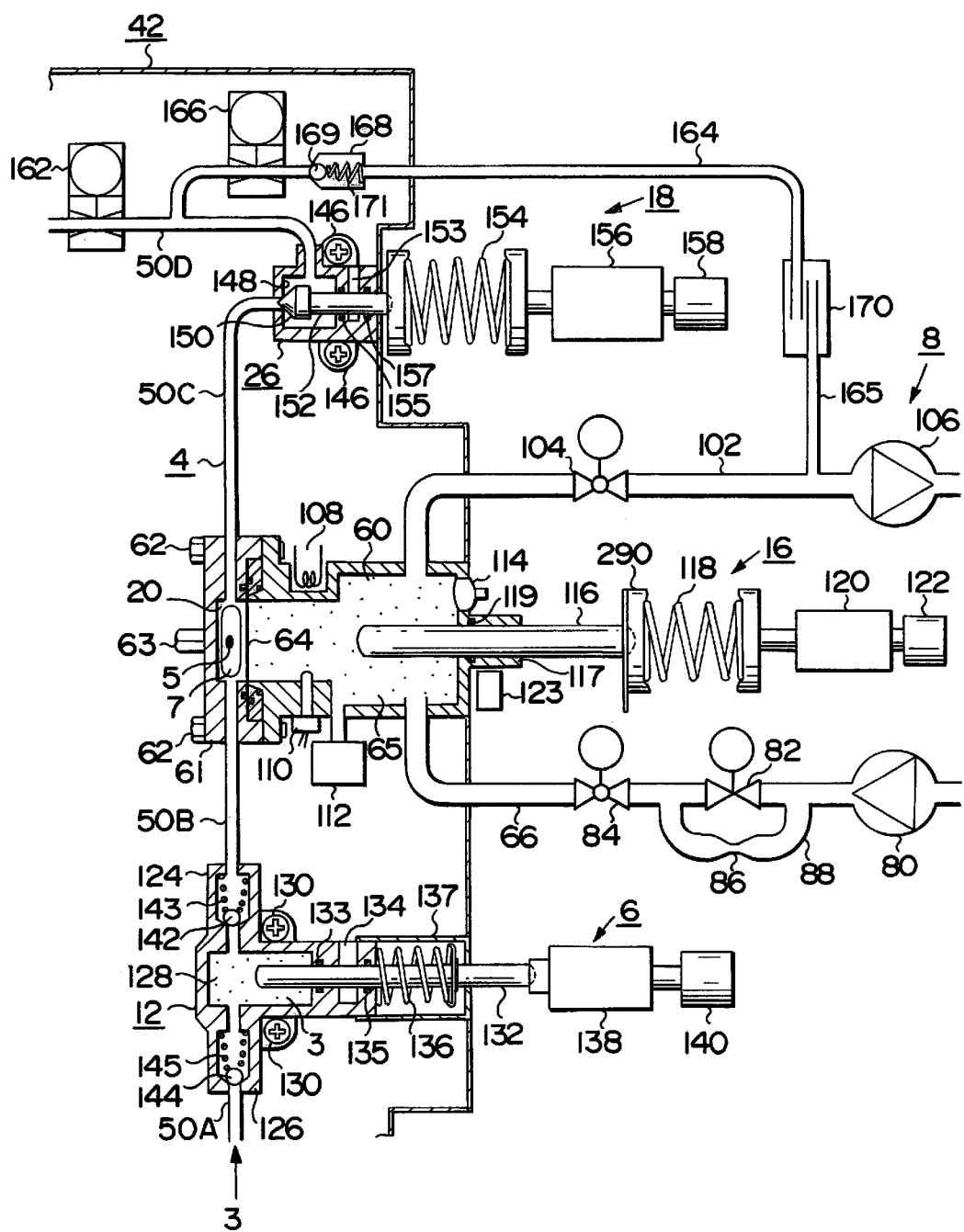
FIG. 3 is an enlarged view of a part of a culture circuit unit, a culture medium supply apparatus, a pressure application apparatus, and a pressure buffering apparatus respectively of the culture apparatus.
Figure 4:
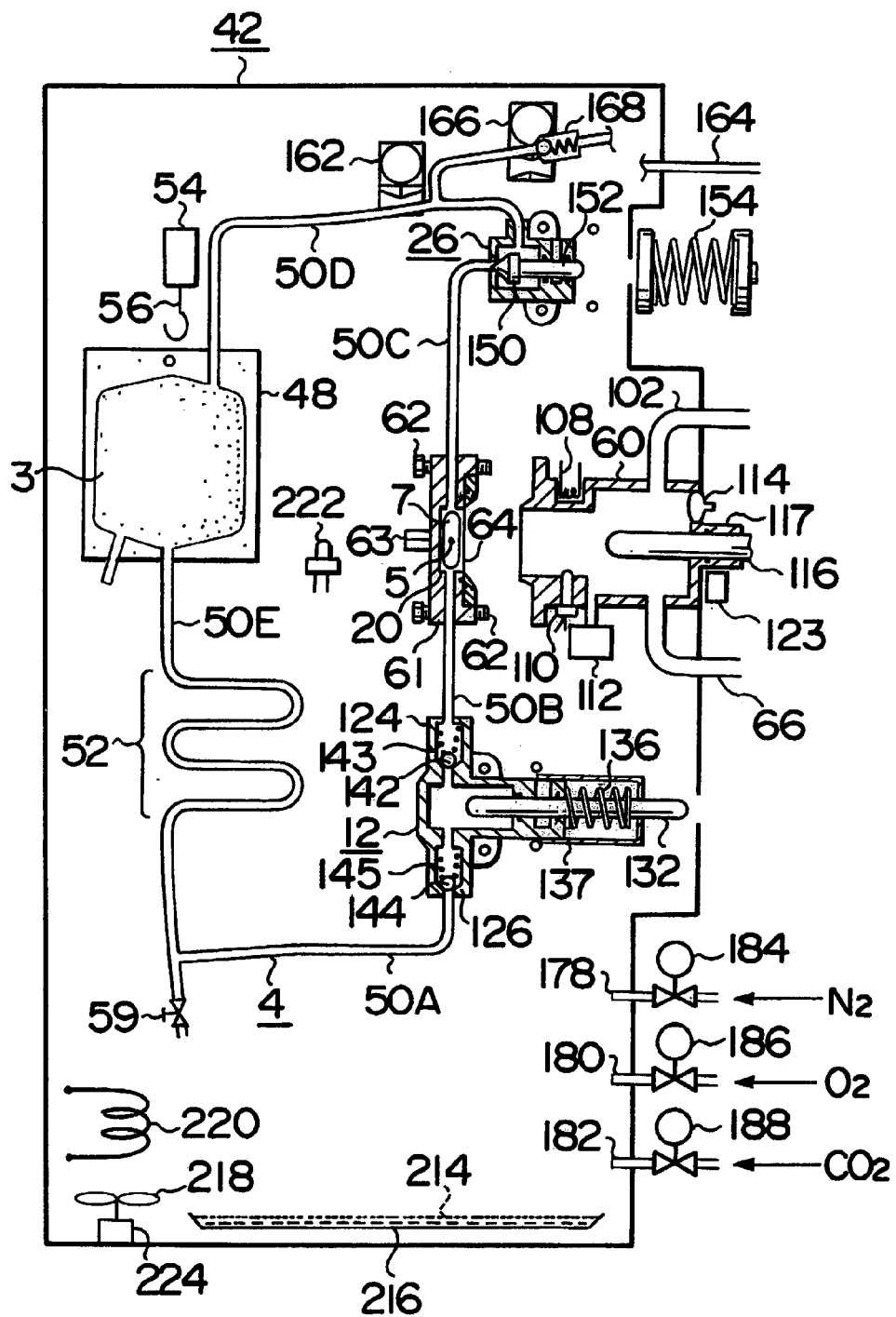
FIG. 4 is a view showing a status where the culture apparatus and the culture circuit unit are separated from each other.

FIG. 2 shows a detailed construction of the culture apparatus 1 and FIG. 3 enlarges a part of the culture circuit unit 4, culture medium supply apparatus 6, pressure application apparatus 16 and pressure buffering apparatus 18 of the culture pressure application apparatus 8 respectively installed in the culture apparatus 1. The culture apparatus 1 is constructed, as shown in FIG. 4, such that the culture circuit unit 4 is detachable from the culture apparatus 1.

The culture apparatus 1 has a culture box 42 that can be hermetically sealed, and the opening and shutting of a door 270 (FIG. 14) is detected by a door switch 44. The culture circuit unit 4 for supplying the culture medium 3 is accommodated in the culture box 42. The culture circuit unit 4 is a detachable tube unit for connecting a culture medium bag 48 serving as a culture medium tank for storing therein the culture medium 3 by way of the culture chamber 20, medium supply apparatus 12, and pressure relief valve 26 by tubes 50A, 50B, 50C, 50D and 50E. The tubes 50A, 50D, 50E constituting gas absorption portion 41 (FIG. 1) are formed of a vent tube made of an elastomer material or the like capable of absorbing gas inside the culture box 42. The tubes 50B and 50C constituting the pressure resistant portion 43 (FIG. 1) are formed of a pressure resistant tube capable of withstanding a pressure of the culture medium 3. A gas absorption portion 52 for absorbing the gas inside the culture circuit unit 4 is formed in the tube 50E by bending the tube 50E.

The culture medium bag 48 is supported by a hook 56 having a detection switch 54 serving as weight detection means on the wall surface of the culture box 42, wherein a volume corresponding to the weight of the culture medium 3 inside the culture medium bag 48 is detected by the detection switch 54. When the detection switch 54 detects the decrease of a predetermined weight of the culture medium bag 48, abnormality is notified by indication means (indication apparatus 232) or telephone or the like by way of the control apparatus 40. A culture medium discharge portion 58 is provided at the branched portion between the tubes 50A and 50E where the medium supply apparatus 12 and gas absorption portion 52 are provided, and it is opened or shut by a checking valve 59. The checking valve 59 is means for collecting the culture medium 3 inside the culture circuit unit 4, and the culture medium 3 collected through the culture medium discharge portion 58 is subjected to an inspection of denaturation, namely, it is inspected whether the culture medium 3 is contaminated by bacteria or the like or subjected to an inspection of pH, concentration, material produced by the culture medium 3, oxygen concentration, carbon dioxide concentration and so forth.

The cell 5 to be cultivated is transplanted in the scaffold 7 formed by collagen or the like and it is accommodated inside the culture chamber 20 together with the scaffold 7. The culture chamber 20 is formed of a culture vessel 61 that is detachably attached to a pressure chamber 60 by fixing means such as a plurality of bolts 62 or the like, and an injection port 63 is provided onto the culture vessel 61. The injection port 63 is used for transplanting the cell 5 to be cultivated in the scaffold 7 provided inside the culture chamber 20 by a syringe or the like. The culture chamber 20 can be attached to the pressure chamber 60 by other fixing means such as a clamper. Both the pressure chamber 60 and culture vessel 61 are sealed by a seal member such as an O ring. The surface of the pressure chamber 60 side of the culture chamber 20 is closed by a pressure transmitting film 64 to form a hermetically sealed space and water 65 (for pressurizing) inside the pressure chamber 60 contacts the culture chamber 20 by way of the pressure transmitting film 64.

The water (fluid) tank for pressurizing 68 is connected to the pressure chamber 60 through a water supply conduit 66, and a flowing water sensor 70, a pump 80, a bypass valve 82, and a seal valve 84 are respectively provided on the water supply conduit 66, wherein a bypass valve 82 is provided on a bypass conduit 88 having an orifice 86 at the middle thereof. That is, when the bypass valve 82 and seal valve 84 are opened to drive the pump 80, when the water 65 (for pressurizing) is filled inside the pressure chamber 60 from the water tank for pressurizing 68. Since a level of pressurized water inside the water tank for pressurizing 68 is detected by a water level sensor 96, when a water supply valve 92 is opened or shut depending on a water level, the water 65 (for pressurizing) can be replenished in the water tank for pressurizing 68 through a water supply conduit 94 so that the water level inside the water tank for pressurizing 68 is always kept in the optimum water level. A water discharge conduit 98 is branched from the water supply conduit 66 of the water tank for pressurizing 68, and the water 65 (for pressurizing) is discharged through the water discharge conduit 98 when a fluid discharge valve 100 is opened when the culture of the cell 5 is completed.

A collection conduit 102 directing toward the water tank for pressurizing 68 is provided in the pressure chamber 60 and there are provided a seal valve 104 and a circulation pump 106 in the collection conduit 102. The tip end of the collection conduit 102 is submerged in the water 65 (for pressurizing) inside the water tank for pressurizing 68. That is, when the seal valve 84 is opened and the bypass valve 82 is shut to drive the circulation pump 106, a pressure inside the pressure chamber 60 is decreased, air bubbles and so fourth that are stuck to inner walls of the pressure chamber 60 and the water supply conduit 66, collection conduit 102 and so forth can be discharged toward the water tank for pressurizing 68 side. Further, the water 65 (for pressurizing) inside the pressure chamber 60 can be supplied from the water tank for pressurizing 68 to the pressure chamber 60 through the water supply conduit 66 when the pump 80, circulation pump 106 are simultaneously driven while it can be returned to the water tank for pressurizing 68 through the collection conduit 102 so that it can be circulated between the pressure chamber 60 and the water tank for pressurizing 68.

A heater 108, a temperature sensor 110, a pressure sensor 112 and a sound producing unit 114 are respectively provided on the wall surface of the pressure chamber 60, wherein heating, temperature and pressure of the water 65 (for pressurizing) accommodated inside the pressure chamber 60 are detected by the temperature sensor 110, pressure sensor 112, and wherein a sound wave such as an ultrasonic wave from the sound producing unit 114 can be applied to the pressure chamber 60, if need be.

A pressure application piston 116 as pressure application means is reciprocatively provided inside the pressure chamber 60 wherein the pressure application piston 116 is supported by a supporter cylinder 117 protruded from the wall surface of the pressure chamber 60, and 0-ring 119 serving as seal means seals between the supporter cylinder 117 and pressure application piston 116. An actuator 120 serving as pressure application driving means and a motor 122 are fixed to the pressure application piston 116 by way of a pressure application spring 118. The motor 122 is formed of, e.g., a stepping motor, and the rotation of the motor 122 is converted into a reciprocating motion by the actuator 120 and the reciprocating motion is applied to the pressure application spring 118 whereby a pressure inside the pressure chamber 60 can be increased or decreased depending on the reciprocating motion of the pressure application piston 116 so that a high pressure is produced when the pressure application piston 116 is moved forward while a low pressure is produced when the pressure application piston 116 is moved backward, and the variation in pressure applies pressure application stimulation to the cell 5 in the scaffold 7 through the pressure transmitting film 64. Further, the position of the pressure application piston 116 is detected by a position sensor 123, and the detected data is used for controlling the reciprocating motion of the pressure application piston 116, namely, the control of pressure application stimulation.

In this case, the water 65 (for pressurizing) is filled in the pressure chamber 60, and a pressure applied by the pressure application piston 116 acts on the entire surface of the pressure transmitting film 64 through the water 65 (for pressurizing), and the same pressure serving as a hydrulic pressure uniformly acts on the cell 5 or tissue through the pressure transmitting film 64 and the culture medium 3, and a strain caused by the same pressure can also act on the cell 5 or tissue. Further, it is possible to allow a dynamic range of the amount of variation in pressure large when controlling the amount of motion of the pressure application piston 116 so as to finely control the pressure from a small value to a large value. The motion of the pressure application piston 116 is detected by the position sensor 123 and is monitored by the control apparatus 40, and when the amount of motion arrives a critical position, an alarm output is outputted from the control apparatus 40 as an abnormality of the culture apparatus 1, then alarm indication is performed on indication means (the indication apparatus 232 in FIG. 5 and so forth) connected to the control apparatus 40 or the abnormality is notified to an administrator through a communication line such as a telephone.

The medium supply apparatus 12 for supplying continuously or intermittently the culture medium to culture chamber 20 includes a medium supply chamber 128 having a supply side check valve 124 and a suction side check valve 126 at the medium input and output side, and it is detachably attached to the culture box 42 by screws 130. A medium supply piston 132 is reciprocatively attached to the medium supply chamber 128, and a disinfectant fluid tank 134 is provided at the middle portion of the medium supply piston 132, while a pressure application spring 136 is attached to the middle portion of the medium supply piston 132. O rings 133, 135 serving as seal means are provided between the medium supply piston 132 and a main body of the medium supply chamber 128. A disinfectant or an antiseptic solution or antibiotic substance such as penicillin is filled in the disinfectant fluid tank 134 to prevent the entrance of bacteria or a foreign matter from the outside. The pressure application spring 136 is accommodated in a protection cylinder 137.

An actuator 138 serving as driving means and a motor 140 are respectively attached to the rear end portion of the medium supply piston 132. The motor 140 is formed of, e.g., a stepping motor and the rotation of the motor 140 is converted into a reciprocating motion by the actuator 138, and the thus converted reciprocating motion is applied to the pressure application spring 136 so that a pressure inside the medium supply chamber 128 increases or decreases in response to the reciprocating motion of the medium supply piston 132. The varied pressure at that time is applied to valve bodies 142, 144 of the supply side check valves 124 and suction side check valve 126. When the medium supply piston 132 is pulled out from the medium supply chamber 128, the inside of the medium supply chamber 128 is negatively pressurized by the amount of pulling out of the medium supply piston 132 so that the valve body 142 is pulled downward by a restoring force of a spring 143 to shut the supply side check valve 124 while the valve body 144 is pulled upward against a pressure application force of a spring 145 to open the suction side check valve 126. As a result, the culture medium 3 is sucked into the medium supply chamber 128. Further, when the medium supply piston 132 moves inside the medium supply chamber 128, the inside of the medium supply chamber 128 is pressurized to lower the valve body 144 so as to shut the suction side check valve 126 while the valve body 142 moves upward to open the supply side check valve 124 so that the culture medium 3 inside the medium supply chamber 128 is supplied to the culture chamber 20 side.

The pressure buffering apparatus 18 for the culture medium 3 has the pressure relief valve 26, and the pressure relief valve 26 is detachably attached to the culture box 42 by screws 146. A valve body 150 which moves back and forth and closable inside the valve chamber 148 is attached to the pressure relief valve 26, a disinfectant fluid tank 153 is provided on the middle portion of a plunger 152 of the valve body 150. O rings 155, 157 serving as seal means are provided between the plunger 152 and a main body of the valve chamber 148. A disinfectant or an antiseptic solution or an antibiotic substance such as penicillin is filled in the disinfectant fluid tank 153 to prevent the entrance of bacteria or a foreign matter from the outside. An actuator 156 serving as driving means and a motor 158 are respectively attached to the rear end portion of the plunger 152 of the valve body 150 by way of a buffer spring 154. The motor 158 is formed of, e.g., a stepping motor and the rotation of the motor 158 is converted into a reciprocating motion by the actuator 156, and the thus converted reciprocating motion is applied to the buffer spring 154 so that an operation pressure for opening the valve body 150 is controlled in accordance with the compression of the buffer spring 154. That is, when the compression of the buffer spring 154 is high, a pressure from the culture medium 3 needed for opening the valve body 150 becomes high while when the compression of the buffer spring 154 is low, a pressure from the culture medium 3 needed for opening the valve body 150 becomes low. The reason why the pressure buffering apparatus 18 is provided is to buffer a pressure application force applied to the culture medium 3 in the culture chamber 20 at the culture circuit unit 4 side.

A pinch valve 162 and a suction tube 164 are branched from a tube 50D for connecting the valve chamber 148 of the pressure relief valve 26 and the culture medium bag 48, and a pinch valve 166, a check valve 168 and a culture medium tank 170 are respectively provided on the suction tube 164, while the culture medium tank 170 is connected to the collection conduit 102 through a suction tube 165. The pinch valve 162 is used for opening and shutting the tube 50D while the pinch valve 166 is used for opening and closing the suction tube 164. A valve body 169 of the check valve 168 is shut by a pressure application force of a spring 171. When a pressure of the culture medium 3 exceeds a pressure application force of the spring 171, the culture medium 3 flows to the culture medium tank 170 side through the suction tube 164. The pinch valve 166 can shut the suction tube 164 by operating it regardless of the check valve 168 so as to prevent the flow of the culture medium 3. Since the culture medium tank 170 serves as a hermetically sealed container when the pinch valve 166 is opened, a pressure inside the culture medium tank 170 is decreased when the circulation pump 106 is driven while closing the seal valve 104 is shut so that the valve body 169 is moved against the pressure application force of the spring 171 to open the check valve 168. At this time, the culture medium 3 can be drawn into the culture medium tank 170 side.

An $N_2$ gas tank 172, an $O_2$ gas tank 174 and a $CO_2$ gas tank 176 serving as the gas mixture/concentration regulating apparatus 36 are respectively connected to the culture box 42 through conduits 178, 180, 182. Gas shutting valves 184, 186, 188, flow control valves 190, 192, 194, flow meters 196, 198, 200, pressure control apparatus 202, 204, 206 and valves 208, 210, 212 are respectively provided on the conduits 178, 180, 182. That is, when the gas closing valves 184, 186, 188 are selectively opened or shut, at least one of $N_2$ gas, $O_2$ gas or $CO_2$ gas is supplied and mixed with each other.

Humidifying water sourcer 216 for storing therein humidifying water 214 serving as a humidity regulating apparatus 32 and a stirring fan 218 are installed in the culture box 42, while a gas heating heater 220 serving as a temperature regulating apparatus 34 as heating means, a box temperature sensor 222 and the stirring fan 218 are also installed in the culture box 42. The stirring fan 218 is driven by a fan motor 224.

Although an alarm is issued when the culture apparatus 1 becomes abnormal, the control apparatus 40 controls a temperature, a gas concentration inside the culture box 42 and continues a medium supply operation so as to hold the cell 5 or tissue under culture regardless of the kind of abnormality until an administrator takes necessary means against the abnormality. The control apparatus 40 also controls a temperature, a gas concentration inside the culture box 42 and continues a medium supply operation even if a predetermined culture time arrives or a normal operation is completed.

Figure 5:
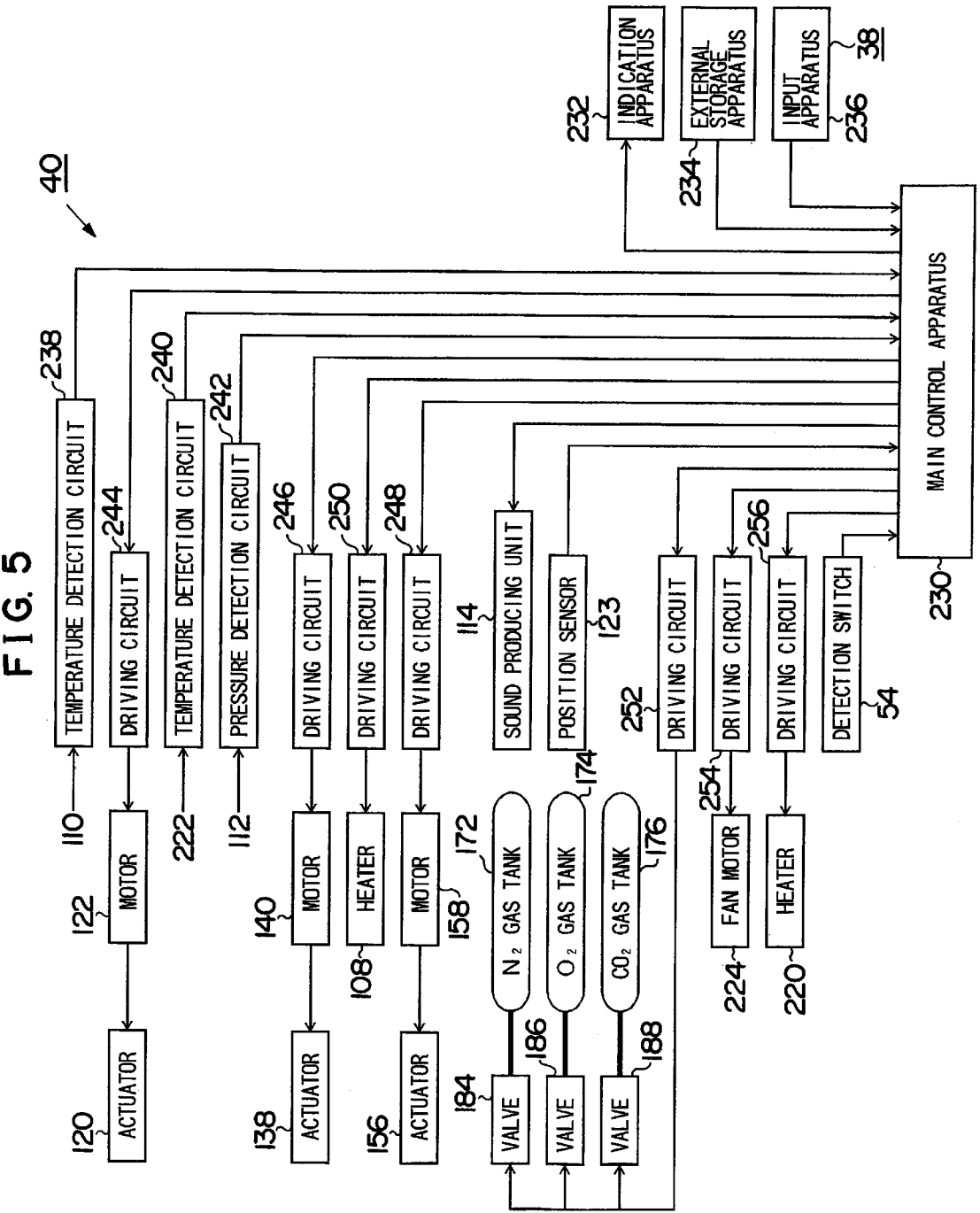
FIG. 5 is a block diagram showing a control apparatus.

FIG. 5 shows the concrete construction of the operation apparatus 38 and control apparatus 40. A main control apparatus 230 is commonly provided in the operation apparatus 38 and control apparatus 40 formed of a personal computer and so forth. An indication apparatus such as a display, liquid crystal, an external storage apparatus 234 such as a hard disc, an optical disc, a floppy disc, an IC card, and a key board input apparatus 236 are respectively connected to the main control apparatus 230. The key board input apparatus 236 constitutes a part of the whole of the operation apparatus 38.

There are applied to the main control apparatus 230 the following, namely, a detection output of the temperature sensor 110 by way of a temperature detection circuit 238, a detection output of the box temperature sensor 222 by way of temperature detection circuit 240, a detection output of the pressure sensor 112 by way of a pressure detection circuit 242, a detection output of the position sensor 123 and a detection output of the detection switch 54 while there are obtained the following respectively by way of the main control apparatus 230, namely, a driving output of the motor 122 by a driving circuit 244, a driving output of the motor 140 by a driving circuit 246, a driving output of the motor 158 by a driving circuit 248, a driving output of the heater 108 by a driving circuit 250, a driving output of the valves 184, 186, 188 by a driving circuit 252, a driving output of the fan motor 224 by a driving circuit 254, a driving output of the heater 220 by a driving circuit 256, and the driving output of the sound producing unit 114.

Figure 6:
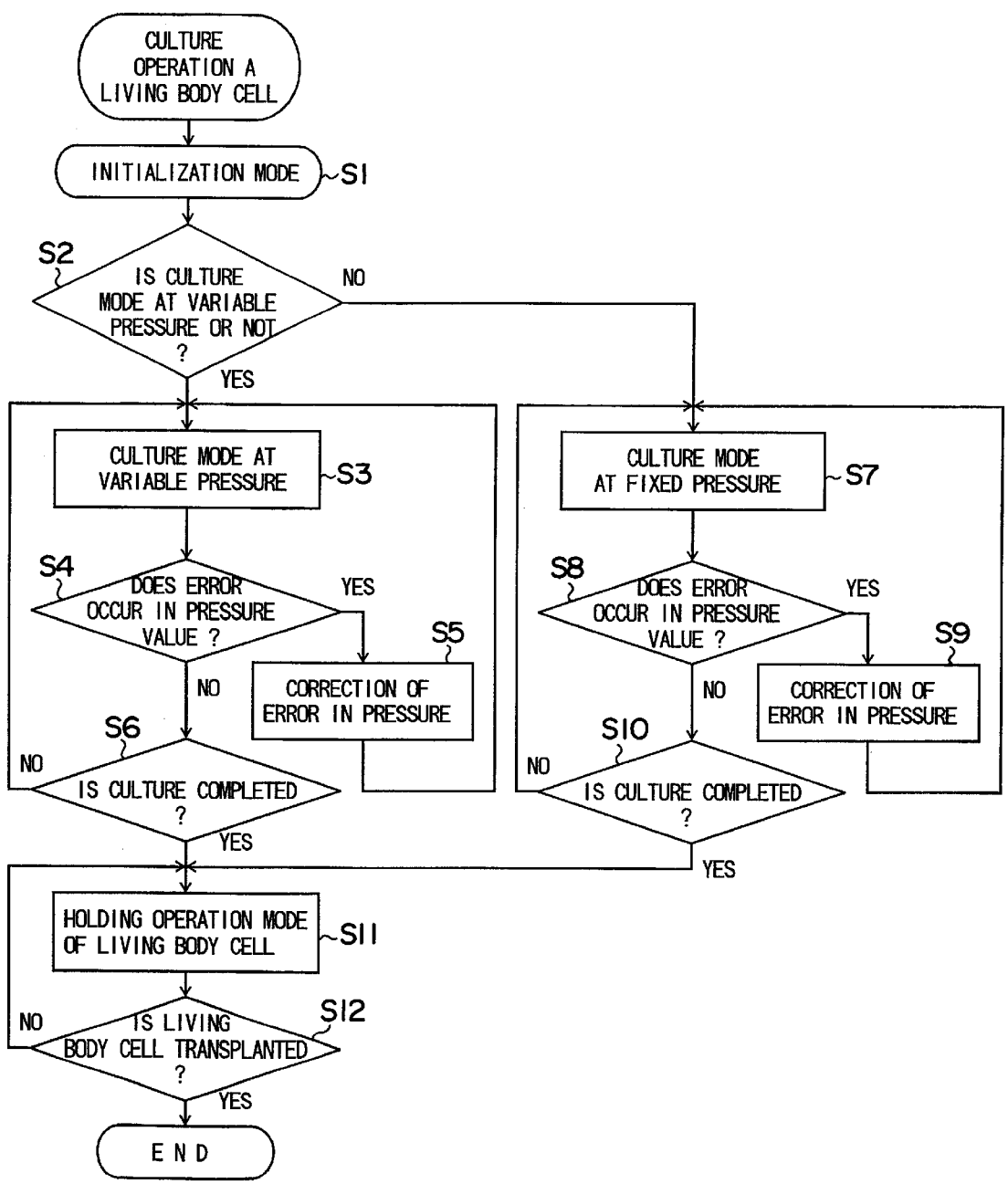
FIG. 6 is a flow chart showing a method of cultivating the cell or tissue according to the invention.

FIG. 6 is a flow chart showing a method of cultivating the cell or tissue according to the invention.

Step S1 is an initialization mode. This initialization mode includes a step of filling the water 65 (for pressurizing) inside the pressure chamber 60 and filling the culture medium 3 inside the culture circuit unit 4 after the culture circuit unit 4 is installed and a step of sampling the amount of operation of the pressure application apparatus 16 of the culture pressure application apparatus 8 and the pressure buffering apparatus 18 corresponding to an inputted set pressure value, and storing the sampled amount of operation in a memory, described later. Elongation percentage of a material constituting the culture circuit unit 4 is different from that of the pressure transmitting film 64, and the amount of operation for obtaining a set pressure is differentiated by the presence of air valves and so forth remaining in the pressure chamber 60. Accordingly, in the initialization mode, these set values are corrected.

When the culture circuit unit 4 is installed, the gas mixture/concentration regulating apparatus 36, humidity regulating apparatus 32 and temperature regulating apparatus 34 are operated, thereby filling gases inside the culture box 42 and regulating humidity and temperature to optimum values. Thereafter, the water 65 (for pressurizing) formed of service water and so forth is replenished in the water tank for pressurizing 68 by opening the water supply valve 92, then the bypass valves 82, seal valves 84 and 104 are opened to operate the pump 80 so that the water 65 (for pressurizing) is supplied inside the pressure chamber 60. The amount of supply of the water 65 (for pressurizing) to the pressure chamber 60 is detected by the flowing water sensor 70, and when a predetermined amount of water 65 (for pressurizing) is detected, the pump 80 is stopped so as to switch to a circulation operation by the circulation pump 106.

In the circulation operation, the bypass valve 82 is shut to switch to the flow to the bypass conduit 88. At this time, the amount of water 65 (for pressurizing) is restricted by the orifice 86 so that the pressure chamber 60 is negatively pressurized by the suction force of the circulation pump 106, and air valves remaining inside the pressure chamber 60 are discharged toward the water tank for pressurizing 68 side. At this time, the pinch valve 162 is shut and the pinch valve 166 is opened so that the culture medium 3 inside the culture medium bag 48 is filled in the culture chamber 20 by the negative pressure produced by the circulation pump 106 through the tubes 50E, 50A, 50B. After the culture medium 3 is filled in the culture chamber 20 by operating the circulation pump 106 for a predetermined time, the pinch valve 166 is shut and the pinch valve 162 and bypass valve 82 are opened to release a negative pressure caused by the circulated flow, then the circulation pump 106 is stopped. Subsequently, after the seal valves 84, 104 are shut, the water 65 (for pressurizing) inside the pressure chamber 60 is heated by the heater 108, and the heated temperature is detected by the temperature sensor 110 to start the control of the temperature.

Then, the motor 158 of the pressure buffering apparatus 18 is operated to shut the pressure relief valve 26 so as to block the tube 50C at a given pressure. When the pressure application apparatus 16 is operated by operating the motor 122 until a predetermined maximum pressure Pmax is detected. When maximum pressure Pmax is detected, the counted number of pulses of the motor 122 is stored in the memory of the main control apparatus 230. Then, the motor 158 of the pressure buffering apparatus 18 is rotated until the present pressure value is decreased, then the counted number of pulses of the motor 158 is stored in the memory of the main control apparatus 230 while the pressure value serves as the position of the maximum pressure Pmax.

Then, the motor 122 of the pressure application apparatus 16 is rotated until a predetermined minimum pressure Pmin is detected. When the minimum pressure Pmin is detected, the counted number of pulses of the motor 122 is stored in the memory of the main control apparatus 230. Subsequently, the motor 158 of the pressure buffering apparatus 18 is rotated, and the motor 158 is stopped at the position where the decrease of a pressure from the minimum pressure Pmin starts. At this time, the counted number of pulses of the motor 158 is stored in the memory of the main control apparatus 230.

Then, after the initialization mode, a program goes to step S2 to determine whether it is a culture mode or not. That is, a pressure is periodically varied to determine whether a culture is to be performed or not, wherein when a pressure variation is to be controlled, the program goes to a culture mode at varied pressure in step S3 while when the culture is performed at a given pressure, the program goes to a culture mode at fixed pressure in step S7.

In the culture mode at varied pressure in step S3, increasing of a pressure, holding of a pressure, increasing of a pressure, and holding of a pressure are repeated every cycle T to pressurize and stimulate the cell 5 in the culture chamber 20 while supplying the culture medium 3 to the cell 5.

In step S4, it is determined whether each error between the pressures caused by the operations of pressure application apparatus 16 and pressure buffering apparatus 18 and the maximum pressure Pmax and minimum pressure Pmin exceeds a predetermined value or not. If there occurs each error exceeding the predetermined value, the program goes to step S5 where the amount of motion of the pressure application apparatus 16 and pressure buffering apparatus 18 conforming to each value of the maximum pressure Pmax and minimum pressure Pmin is sampled, thereby correcting a value stored in the main control apparatus 230.

Then in step S6, the programs in steps S3 to S6 are repeated until a predetermined culture time t elapses while when the predetermined culture time t elapsed, the culture is completed, and the program goes to step S11.

In the culture mode at fixed pressure in step S7, the cell 5 or tissue is stimulated by a given pressure and the culture medium 3 is supplied. That is, in step S8, it is determined whether an error between a pressure caused by the operation of the pressure application apparatus 16 and pressure buffering apparatus 18 and a set pressure Ps exceeds a predetermined value or not. If there occurs an error exceeding the predetermined value, the programs goes to step S9 where the amount of motion of the pressure application apparatus 16 and pressure buffering apparatus 18 conforming to the set pressure Ps is sampled, thereby correcting a value stored in the main control apparatus 230. In step S10, when the predetermined culture time t elapses, the culture is completed, and the program goes to step S11.

Thereafter in step S11, a living body cell holding operation mode is performed. Even if the culture of the cell 5 or tissue is completed or tissue is created, it is necessary to hold the cell 5 or tissue soundly for a while until the transfer of the cell 5 or tissue for transplantation is started. In the living body cell holding operation mode, the culture medium 3 is supplied to the cell 5 to keep the living body cell in a sound state while maintaining the cell 5 at a predetermined temperature.

Then, in step S12, it is determined whether the living body cell is transplanted or not, namely, an operation stop instruction for transplanting a tissue formed of the cell 5 is inputted or not, and the circulation of the culture medium 3 and the control of temperature are stopped in response to the operation stopping instruction. Thereafter, the culture circuit unit 4 is detached from the culture apparatus 1 and the cell 5 or tissue is transferred together with the culture circuit unit 4.

Figure 7:
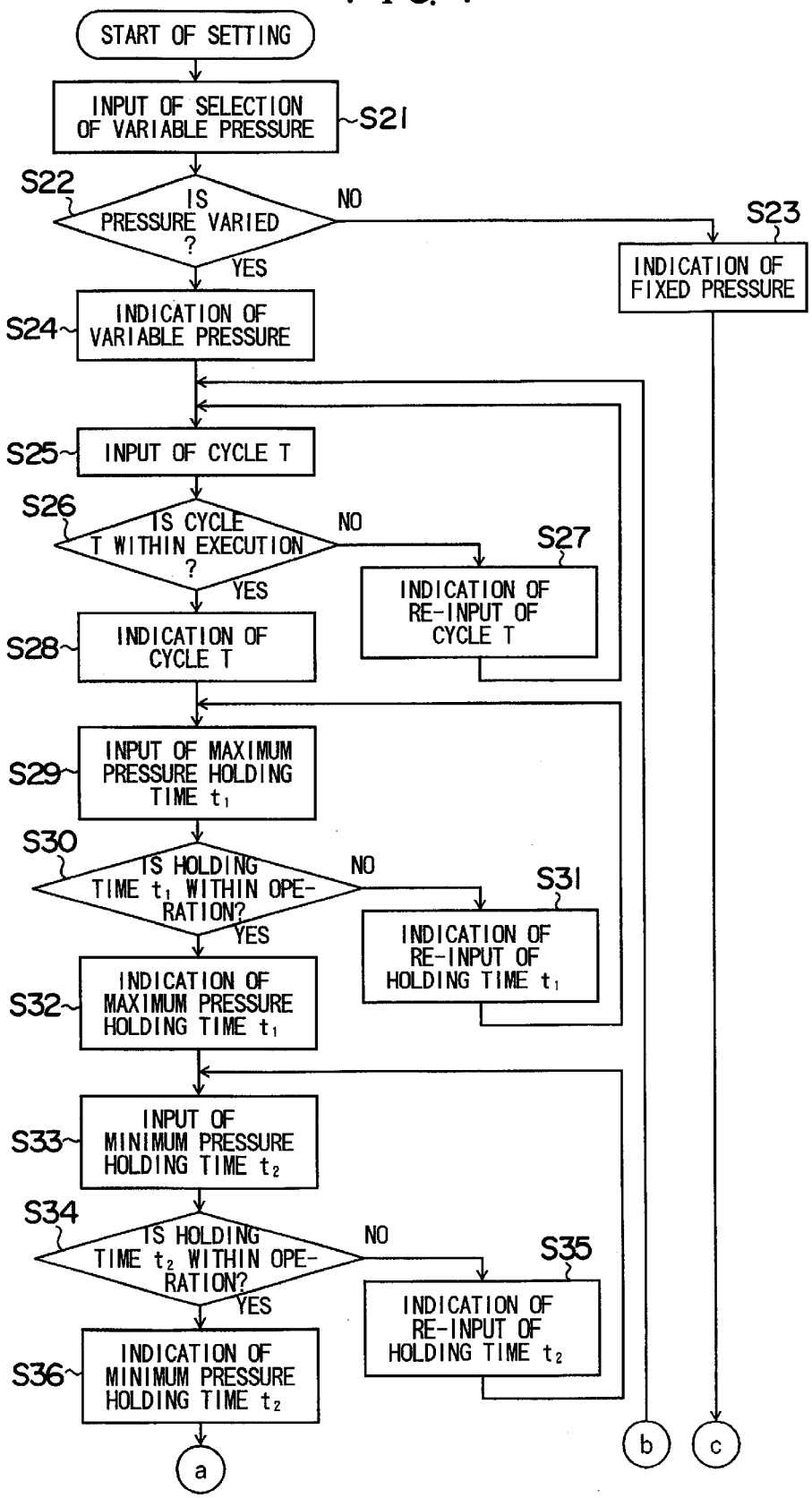
FIG. 7 is a flow chart showing initialization in the method of cultivating the cell or tissue according to the invention.
Figure 8:
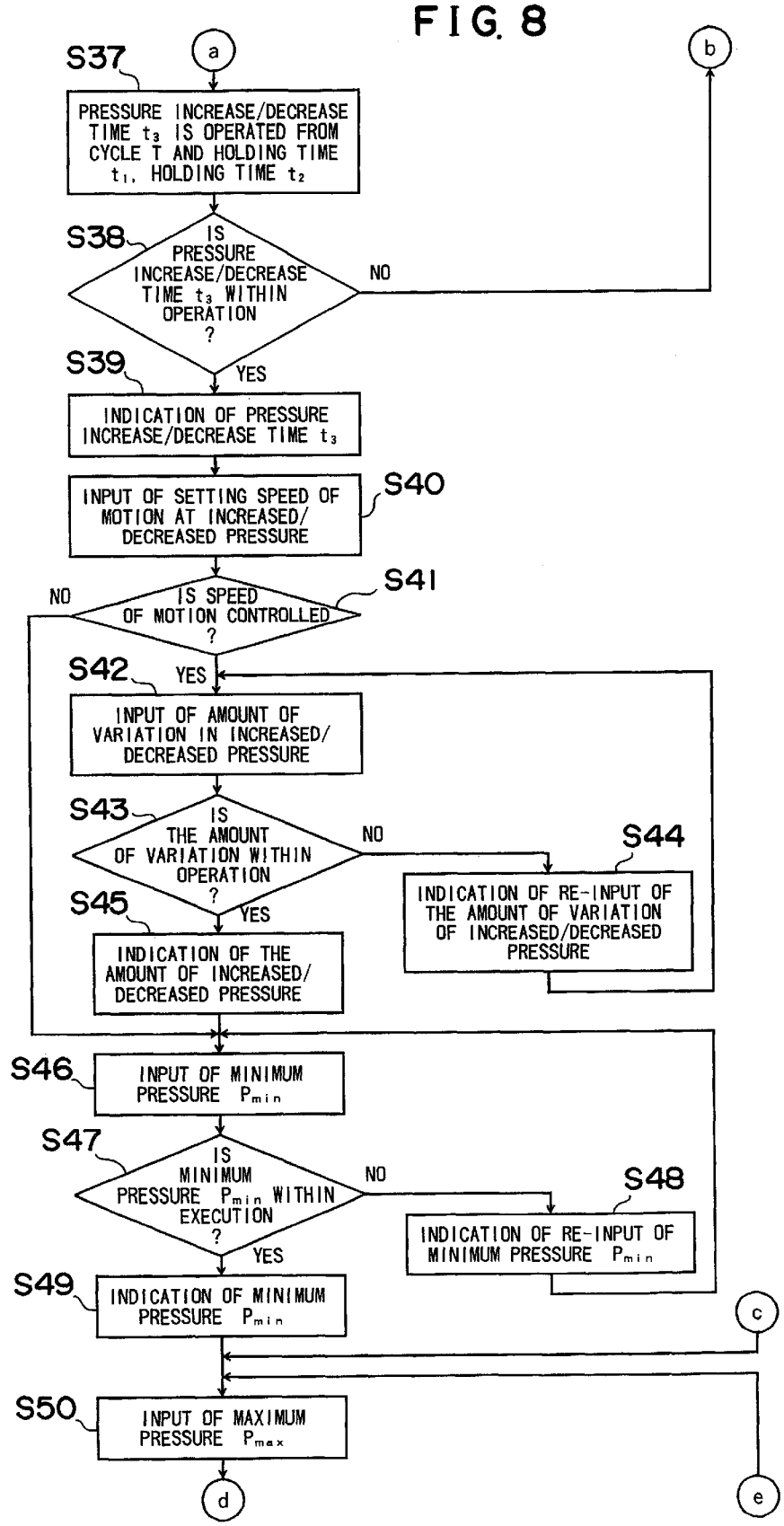
FIG. 8 is a flow chart continued from FIG. 7 showing initialization in the method of cultivating the cell or tissue according to the invention.
Figure 9:
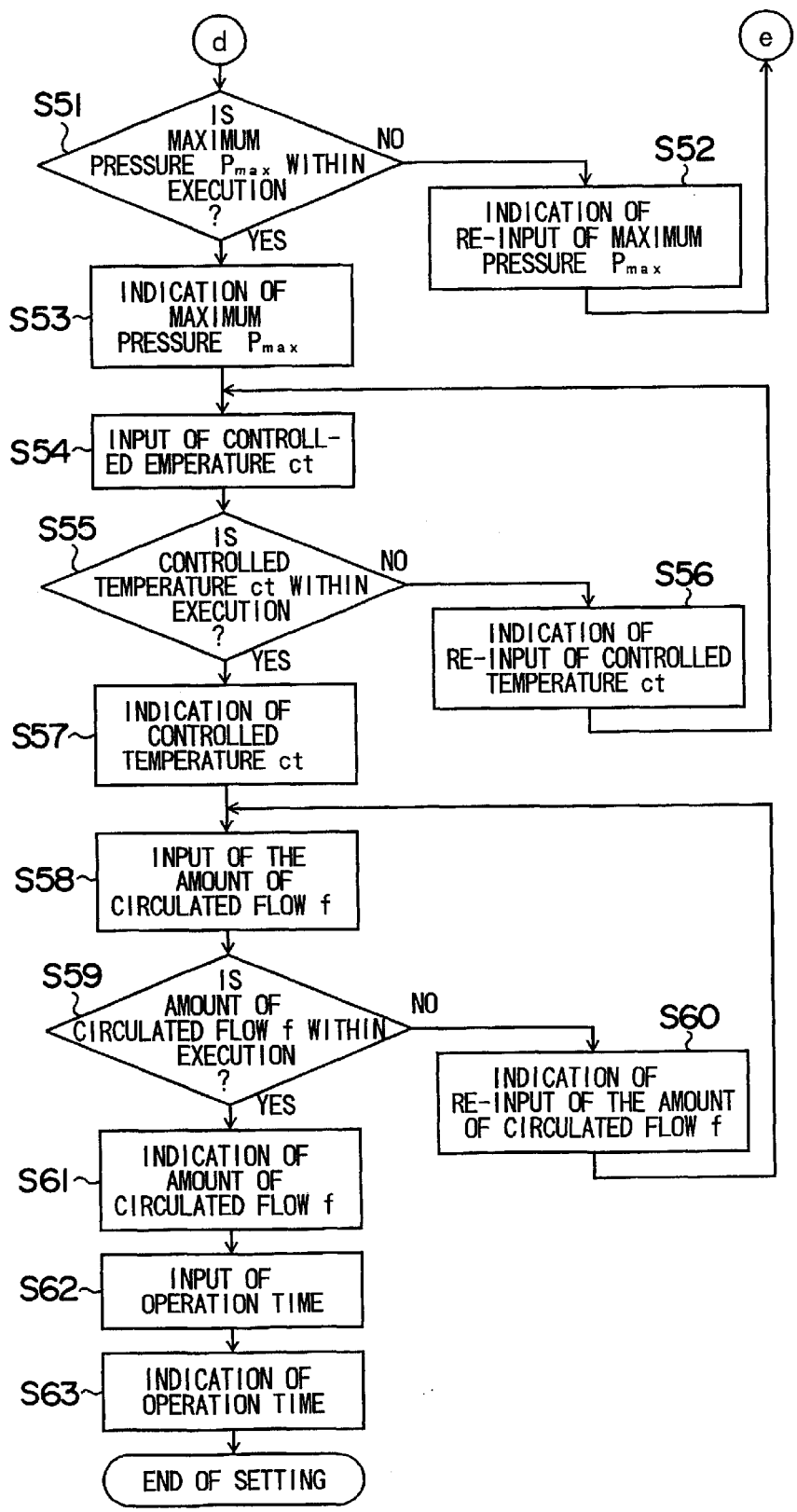
FIG. 9 is a flow chart continued from FIG. 8 showing initialization in the method of cultivating the cell or tissue according to the invention.

FIGS. 7, 8, and 9 show a set inputting operation in the initialization mode, wherein numerals a, b, c, d and e are used as connection symbols of the divided flow charts, wherein the same or conformed letters of a to e extending over two pages are connecting portions.

In step S21, it is inputted that the cell 5 or tissue is cultivated in the culture chamber 20 in a periodically pressurized state or at a fixed pressure. In step S22, when a pressure is varied periodically, the program goes to step S24 where "the variable pressure" is indicated. On the other hand, if the culture is performed under a fixed pressure, the program goes to step S23 where "fixed pressure" is indicated.

In step S25, a cycle T for varying a pressure is indicated. In step S26, it is determined whether the inputted cycle T is within execution or not. If the cycle T is beyond execution, the program goes to step S27 where "re-input of cycle T" is indicated and notified, then the program goes to step S25 where the cycle T is re-inputted. If the cycle T is within execution, the program goes to step S28 where "cycle T" is indicated and it is stored in a memory of the main control apparatus 230.

In step S29, holding time $t_1$ of the maximum pressure Pmax is inputted. In step S30, it is determined whether the holding time $t_1$ is within the operation of the cycle T or not. If the holding time $t_1$ is beyond the operation of the cycle T, the program goes to step S31 where "re-input of holding time $t_1$" is indicated and notified, then the program goes to step S29 where the holding time $t_1$ is re-inputted. If the holding time $t_1$ is within the operation of the cycle T, the program goes to step S32 where "holding time $t_1$ of maximum pressure" is indicated and stored in the memory of the main control apparatus 230.

In step S33, holding time $t_2$ of the minimum pressure Pmin is inputted. In step S34, it is determined whether the inputted holding time t2 is within the operation of the cycle T or not. If the holding time $t_2$ is beyond the operation of the cycle T, the program goes to step S35 where "re-input of holding time $t_2$" is indicated and the program goes to step S33 where the holding time $t_2$ is re-inputted. If the holding time $t_2$ is within the operation of the cycle T, the program goes to step S36 where "holding time $t_2$ of minimum pressure" is indicated and stored in the memory of the main control apparatus 230.

In step S37, the inputted cycle T and the difference between times ($t_1$+$t_2$) are halved to operate pressure increasing/decreasing time $t_3$. In step S38, it is determined whether the pressure increasing/decreasing time $t_3$ is within operation or not. If the pressure increasing/decreasing time $t_3$ is beyond operation, it is determined that the values of the cycle T, holding time t1 and holding time $t_2$ are not appropriate, and the program returns to step S25. If the pressure increasing/decreasing time $t_3$ is within operation, the operated pressure increasing/decreasing time t3 is stored in the memory of the main control apparatus 230, and in step S39, "pressure increasing/decreasing time $t_3$" is indicated. In step S40, it is inputted whether the speed of motion is varied or not when increasing or decreasing pressure. The program goes to step S42 when the speed of motion is controlled in step S41 while the program goes to step S46 when the speed of motion is not varied.

In step S42, the amount of variation for controlling the speed of motion when increasing or decreasing a pressure is inputted. In step S43, it is determined whether the inputted amount of variation is operable or not. If inoperable, the program goes to step S44 where "re-input of the amount of variation in amount of increased/decreased pressure" is indicated, and the program goes to step S42 where it is re-inputted. If operable, the program goes to step S45 where "amount of increased/decreased pressure" is indicated and it is stored in the memory of 230. At this time, the displacement of a pressure may be indicated on a simulation picture.

In step S46, the minimum pressure Pmin is inputted. In step S47, it is determined whether the minimum pressure Pmin is within execution or not. If the minimum pressure Pmin is beyond execution, the program goes to step S48 where "re-input of minimum pressure Pmin" is indicated and the program goes to step S46 where the minimum pressure Pmin is re-inputted. On the other hand, if the minimum pressure Pmin is within execution, the program goes to step S49 where "minimum pressure Pmin" is indicated and stored in the memory of the main control apparatus 230.

In step S50, the maximum pressure Pmax is inputted. In step S51, it is determined whether the maximum pressure Pmax is within execution or not. If the maximum pressure Pmax is beyond execution, the program goes to step S52 where "re-input of maximum pressure Pmax" is indicated and the program goes to step S50 where the maximum pressure Pmax is re-inputted. On the other hand, if the maximum pressure Pmax is within execution, the program goes to step S53 where "maximum pressure Pmax" is indicated and stored in the memory of the main control apparatus 230.

In step S54, a controlled temperature ct of the pressure chamber 60 is inputted. In step S55, it is determined whether the controlled temperature ct is within execution or not. If controlled temperature ct is beyond execution, the program goes to step S56 where "re-input of controlled temperature ct" is indicated and the program goes to step S54 where the controlled temperature ct is re-inputted. If the controlled temperature ct is within execution, the program goes to step S57 where "controlled temperature ct" is indicated and is stored in the memory of the main control apparatus 230.

In step S58, the amount of circulated flow f of the culture medium 3 in the culture circuit unit 4 is inputted. In step S59, it is determined whether the amount of circulated flow f is within execution or not. If the amount of circulated flow f is beyond the execution, the program goes to step S60 or "re-input of the amount of circulated flow f" is indicated and notified, then the program goes to step S58 where the amount of circulated flow f is re-inputted. If the amount of circulated flow f is within execution, the program goes to step S61 where "amount of circulated flow f" is indicated and is stored in the memory of the main control apparatus 230. In step S62, the operation time is inputted.

In step S63, "operation time" is indicated and is stored in the memory of the main control apparatus 230.

Described hereinafter is the relation between the pressure application piston 116 in the pressure application apparatus 16 and a pressure applied to the cell 5 or tissue.

Since a force F is expressed by F=P×A, where A (cm$^2$) is a sectional area of the pressure application piston 116, P (kg/cm$^2$) is a pressure and F (kgf) is a force, and the force F is further expressed by F=K×$L_2$, where K (kgf/mm) is a spring constant of the pressure application spring 118 and $L_2$(mm) is the amount of contraction of a spring, the following equation is established.

$$K \times L_2 = P \times A$$

$$L_2 = (P \times A)/K \qquad (1)$$

That is, when the pressure application piston 116 is moved, elasticity of the pressure application spring 118 acts on the pressure application piston 116 so that the pressure application piston 116 compresses the water 65 (for pressurizing) inside the pressure chamber 60. A pressure inside the pressure chamber 60 increases when the water 65 (for pressurizing) is compressed therein, and the increased pressure is detected by the pressure sensor 112. The relation between the displacement of the pressure application piston 116, i.e., the amount of motion (mm) and the pressure P (kg/cm$^2$) becomes e.g., as shown in FIG. 10. In FIG. 10, $L_1$ is the amount of motion by the motor 122, $L_2$ is the amount of contraction of the pressure application spring 118, $L_3$ is the amount of motion of the pressure application piston 116 when the pressure application spring 118 is not used, $L_4$ is the amount of motion of the pressure application piston 116 caused by the shrinkage of mixed air, $L_5$ is the amount of motion of the pressure application piston 116 caused by shrinkage of water and $L_6$ is the amount of motion of the pressure application piston 116 caused by the deformation of a vessel of the culture chamber 20 and pressure chamber 60. $L_3$ is the sum total of $L_4$, $L_5$ and $L_6$, and $L_1$ is the sum total of $L_2$ and $L_3$. The relation between the amount of motion of the pressure application piston 116 in the pressure application apparatus 16 and the value of pressure detected by the pressure sensor 112 is stored in the memory of the main control apparatus 230. The amount of motion of the pressure application piston 116 caused by compression of air is described now.

Since a volume Va of air is expressed by Va=V/(Pa+1), where V (cm$^3$) is a volume of air (at 1 atm.), Va (cm$^3$) is the volume of air (when pressurized) and 1×V=(Pa+1)×Va=constant is fixed while the amount of motion $L_4$ (mm) of the pressure application piston 116 caused by compression of air is expressed as follows.

$$L_4 = 10 \times \{(V - Va)/A\} \qquad (2)$$
$$= [\{V - V(Pa + 1)\}/A] \times 10$$

Further, the amount of motion of the pressure application piston 116 caused by compression of water and culture medium 3 becomes as follows. That is, since the amount of compression ΔW (cm$^3$) of water and culture medium 3 is expressed by ΔW=0.44×10$^{-5}$×P×W where W (cm$^3$) is the volume of water and culture medium 3 and the amount of compression of water (40° C.) is 0.44×10$^{-5}$ (cm$^2$/kg), and hence the amount of motion $L_5$ (mm) of the pressure application piston 116 caused by compression of water and culture medium 3 is expressed as follows.

$$L_5 = \Delta W / A \times 10 \qquad (3)$$
$$= 10 \times \{(0.44 \times 10^{-5} \times P \times W)/A\}$$

The amount of contraction ΔWt is expressed by ΔWt= W×Ct where apparent contraction percentage caused by the deformation of the pressure vessel 22 and culture vessel 61 is Ct, and hence the amount of motion $L_6$ (mm) of the pressure application piston 116 caused by the deformation of the pressure vessel 22 is expressed as follows.

$$L_6 = (\Delta Wt/A) \times 10 \qquad (4)$$
$$= 10 \times \{(W \times Ct)/A\}$$

Accordingly, the total amount of motion of the pressure application piston 116 becomes the value $L_1$ obtained by adding each amount of motions of the pressure application piston 116 in the expressions (1), (2), (3) and (4).

Figure 11:
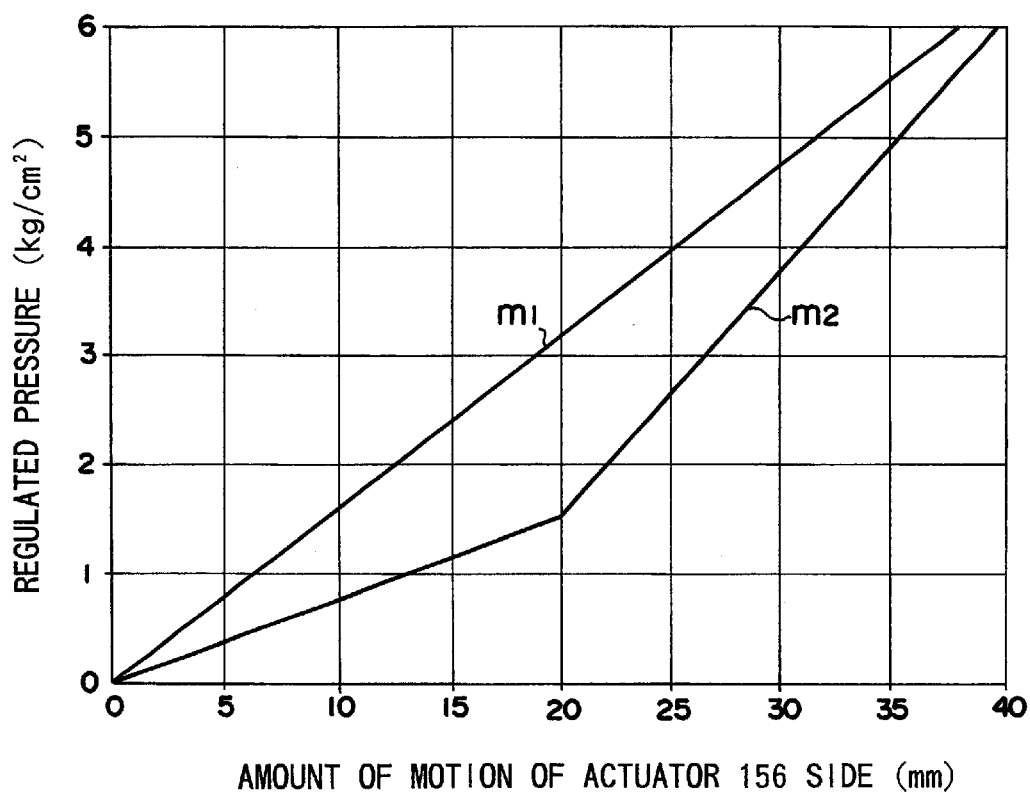
FIG. 11 is a view showing a pressure of a adjustable valve relative to a displacement of an actuator in a pressure relief valve.
Figure 12:
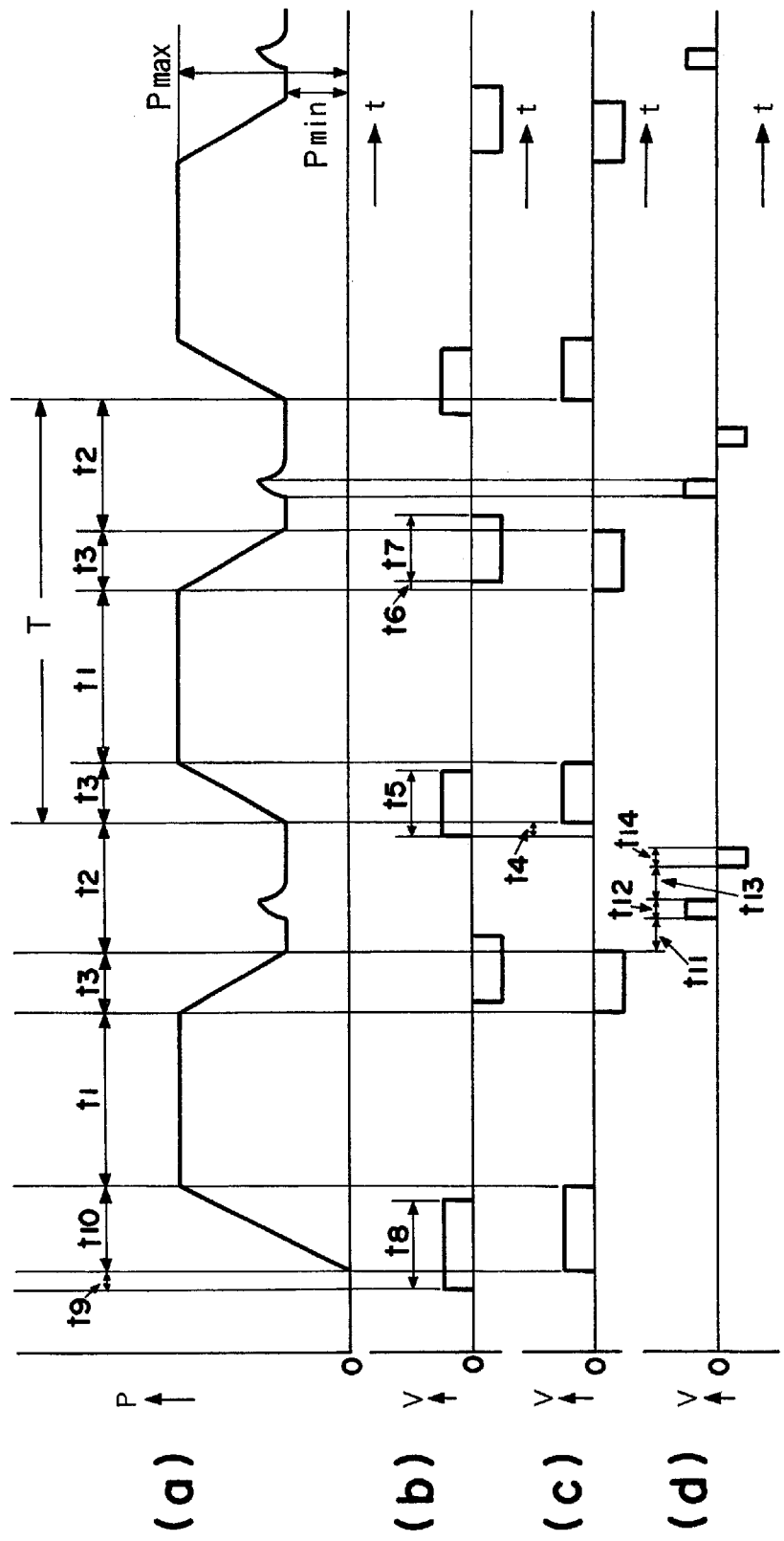
FIG. 12 is a timing chart showing the execution a culture mode at a variable pressure.
Figure 13:
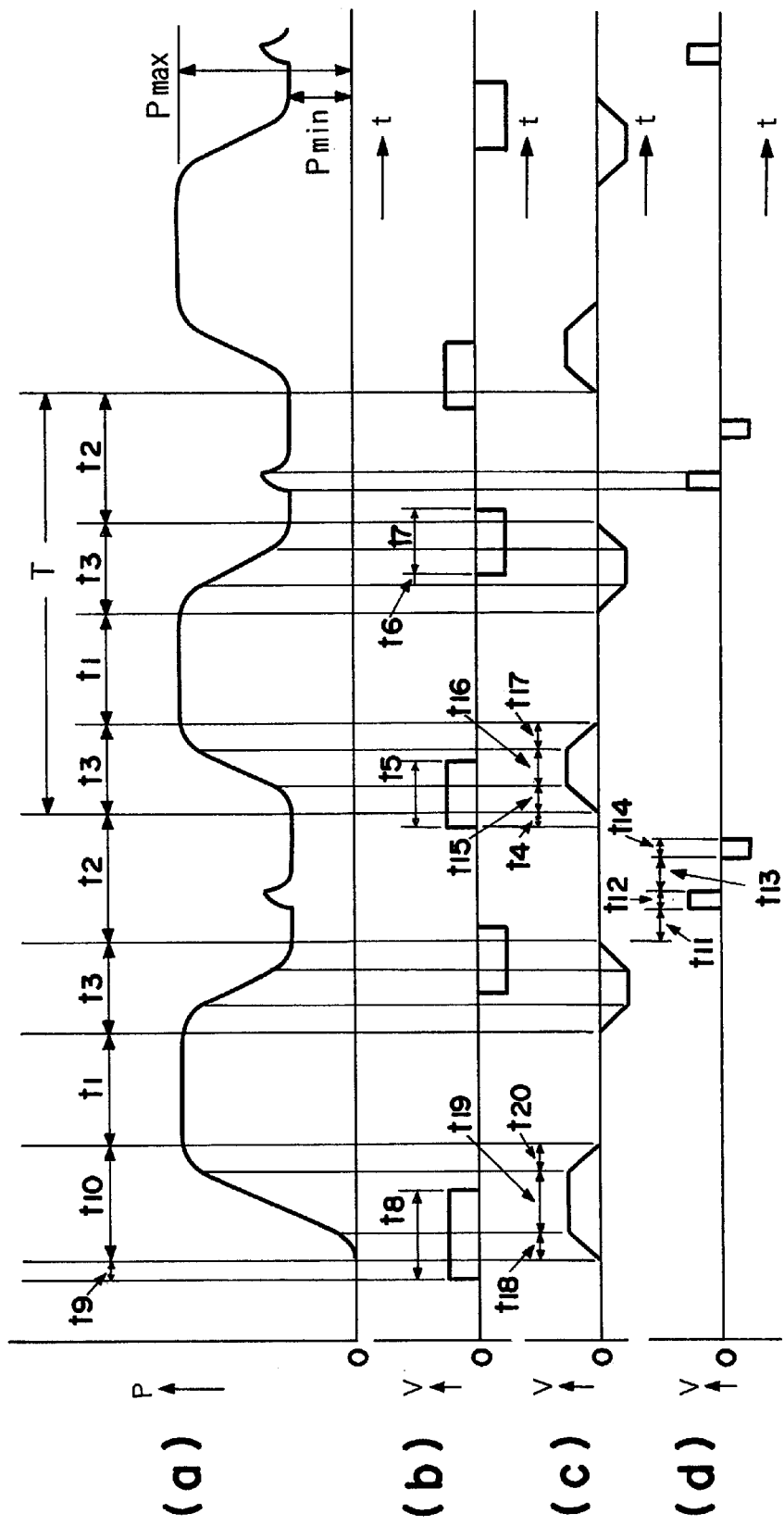
FIG. 13 is a timing chart showing another execution of a culture mode at the variable pressure.

If a pressure applied to the buffer spring 154 is decreased at the pressure buffering apparatus 18 side, a pressure inside the culture chamber 20 exceeds a pressure applied to the pressure relief valve 26 so that the pressure relief valve 26 is opened through which the culture medium 3 passes, and hence a pressure at the culture chamber 20 side is decreased. If a pressure application force of the buffer spring 154 is balanced with a pressure at the culture medium 3 side, the pressure is settled. A pressure applied to the pressure relief valve 26 of the pressure buffering apparatus 18 is described now. A force F balanced with the pressure P is expressed by F=P×B where a blocked area by the pressure relief valve 26 is B (cm$^2$), a pressure is P (kg/cm$^2$), the force balanced with the pressure P is F (kgf), and the balanced force F is also expressed by F=K×m and the amount of contraction m of the buffer spring 154 is expressed by m=P×B/K where a spring constant of the buffer spring 154 is K (kgf/mm) and the amount of shrinkage of the buffer spring 154 is m(mm). FIG. 11 shows a relation between a pressure applied to the pressure relief valve 26 side, namely, the amount of motion of the actuator 156 side (amount of contraction of the buffer spring 154) and a pressure acting on the pressure relief valve 26, namely, controlled pressure. In FIG. 11, a line $m_1$ shows a case where a single buffer spring 154 is used, and a line $m_2$ shows a case where two different buffer springs are used.

Since the capacity of the medium supply apparatus 12 is small, it is possible to substantially neglect the shrinkage of the culture medium 3, deformation of the vessel, and shrinkage of a gas, and so forth. Accordingly, the amount of motion I is expressed by I=V/C because the amount of supply of medium V (ml) of the medium supply piston 132 is expressed by V=C×I where a sectional area of the medium supply piston 132 is C (cm$^2$) and the amount of motion is I (cm) so that the amount of motion is determined by the amount of supply of medium. If the amount of motion of the medium supply piston 132 of the medium supply apparatus 12 is large, the medium supply piston 132 is returned to an original position after it is moved while if the amount of motion of the culture medium 3 is small, the medium supply piston 132 is not returned to the original position but it is moved further from that position during the medium supply operation, then it is returned to the original position after it is moved to an unmovable position. At this time, if a pressure is higher than an allowable value of a set decreased pressure, data between the amount of the motion of the actuator 156 of the pressure relief valve 26 and a pressure that is stored before the operation is corrected to an original value.

FIGS. 12(a) to 12(d) show the manner of execution of the culture mode at a variable pressure to be executed in step S3 in FIG. 6, namely, FIG. 12(a) shows a state of pressure applied to the culture chamber 20 and FIGS. 12(b) to 12(d) show pressure application timings. That is, FIG. 12(a) shows the change or variation in pressure, FIG. 12(b) shows an operation timing of the pressure buffering apparatus 18, FIG. 12(c) shows a pressure application timing of the pressure application apparatus 16, and FIG. 12(d) shows a medium supply timing of the culture medium supply apparatus 6.

In the culture chamber 20, the increase and decrease of a pressure is repeated between the maximum pressure Pmax and minimum pressure Pmin at the cycle T. Each $t_1$ shows time for holding the maximum pressure Pmax while each $t_2$ shows time for holding the minimum pressure Pmin, and each $t_3$ shows operation time when increasing or decreasing a pressure. These maximum pressure Pmax, minimum pressure Pmin, times $t_1$, $t_2$, $t_3$ can be arbitrarily changed depending on the position in the living body where the cell 5 is cultivated in vitro. Further, it is possible to increase or decrease a pressure by selecting appropriate numerical values based on data relating to an age, a sex, a height, a weight respectively of a living body, a position in the living body relating to the cell 5 to be cultivated.

The pressure buffering apparatus 18 blocks the tube 50C by operating the pressure application apparatus 16 so that the pressure application apparatus 16 reaches a position where the maximum pressure Pmax is obtained at the maximum speed for time $t_5$ before the start of pressure application. Thereafter, the operation of the pressure application apparatus 16 is started upon elapse of delay time $t_4$ where a pressure application is performed to extend from the minimum pressure Pmin to the maximum pressure Pmax at the speed corresponding to time $t_3$.

After the maximum pressure Pmax is held for time $t_1$, the pressure application apparatus 16 is re-operated to start the decrease of pressure to extend from the maximum pressure Pmax to minimum pressure Pmin at the speed corresponding to time $t_3$. The pressure buffering apparatus 18 is operated only for time $t_7$ while delayed by time $t_6$ after the pressure application apparatus 16 is operated so as to release the blocking of the tube 50C.

When the control of a pressure is started, a pressure is increased from a pressure close to zero pressure to the maximum pressure Pmax. At this time, the pressure buffering apparatus 18 is moved to a blocking position at the maximum speed while operating the pressure application apparatus 16 upon elapse of time $t_9$, and a pressure application is performed for time $t_8$ until it reaches the maximum pressure Pmax at the speed corresponding to time $t_3$.

The culture medium supply apparatus 6 operates for time $t_{12}$ upon elapse of time $t_{11}$, after holding the minimum pressure Pmin so as to supply the culture medium 3 to the culture chamber 20. It is possible to arbitrarily set the amount of supply of medium by changing the time $t_{12}$.

The medium supply piston 132 is moved backward for time $t_{14}$ substantially equal to time $t_{12}$ upon elapse of the time $t_{13}$ after the supply of medium. In this example, the medium supply is performed for the holding time $t_2$ of the minimum pressure Pmin, but it can be performed for a period of holding time $t_1$ of the maximum pressure Pmax or for a period of pressure increasing and decreasing time $t_3$.

FIGS. 13(a) to 13(d) show the manner of execution of another culture mode at a variable pressure to be executed in step S3 in FIG. 6, namely, FIG. 13(a) shows a state of pressure applied to the culture chamber 20 and FIGS. 13(b) to 13(d) show pressure application timings. That is, FIG. 13(a) shows the change or variation in pressure, FIG. 13(b) shows an operation timing of the pressure buffering apparatus 18, FIG. 13(c) shows a pressure application timing of the pressure application apparatus 16, and FIG. 13(d) shows a medium supply timing of the culture medium supply apparatus 6.

In this example, a pressure pattern is obtained by controlling the variation in pressure by varying a pressure increasing speed and pressure decreasing speed in quadratic function for pressure increasing/decreasing time $t_3$ and the pressure pattern is outputted, so that the pressure pattern applied to cartilage of knees when walking is reproduced because the variation in pressure is controlled. In this case, the pressure application apparatus 16 is varied in an operation speed as shown in FIG. 13(C) for times $t_{15}$, $t_{16}$, $t_{17}$, and the control of the variation in pressure is added to the pressure application force for time $t_3$. The other operations are the same as those shown in FIG. 12, and hence the explanation thereof is omitted.

Second Embodiment (FIGS. 14 to 21)

Figure 14:
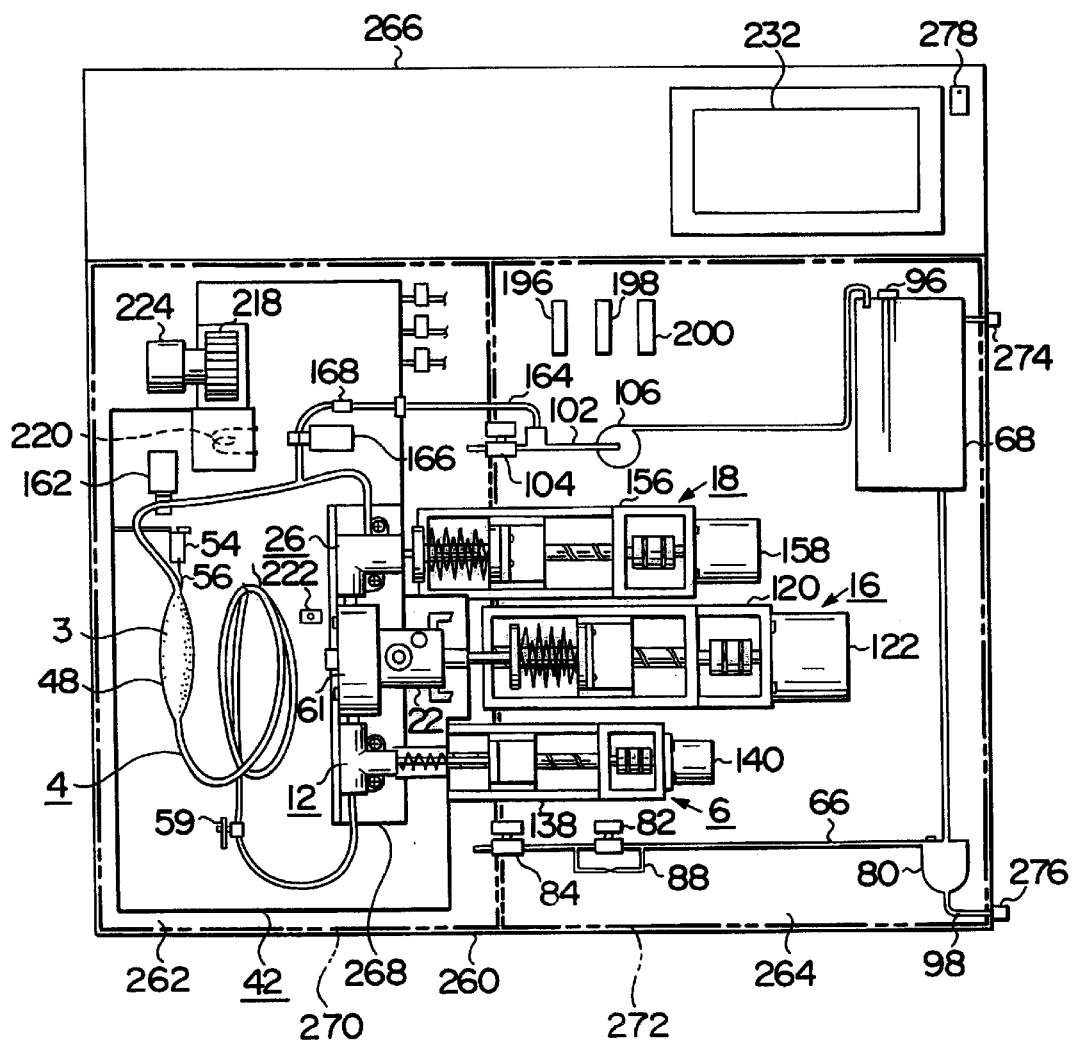
FIG. 14 is a front view of a culture apparatus in a method of and an apparatus for cultivating a cell or tissue according to a second embodiment of the invention.
Figure 15:
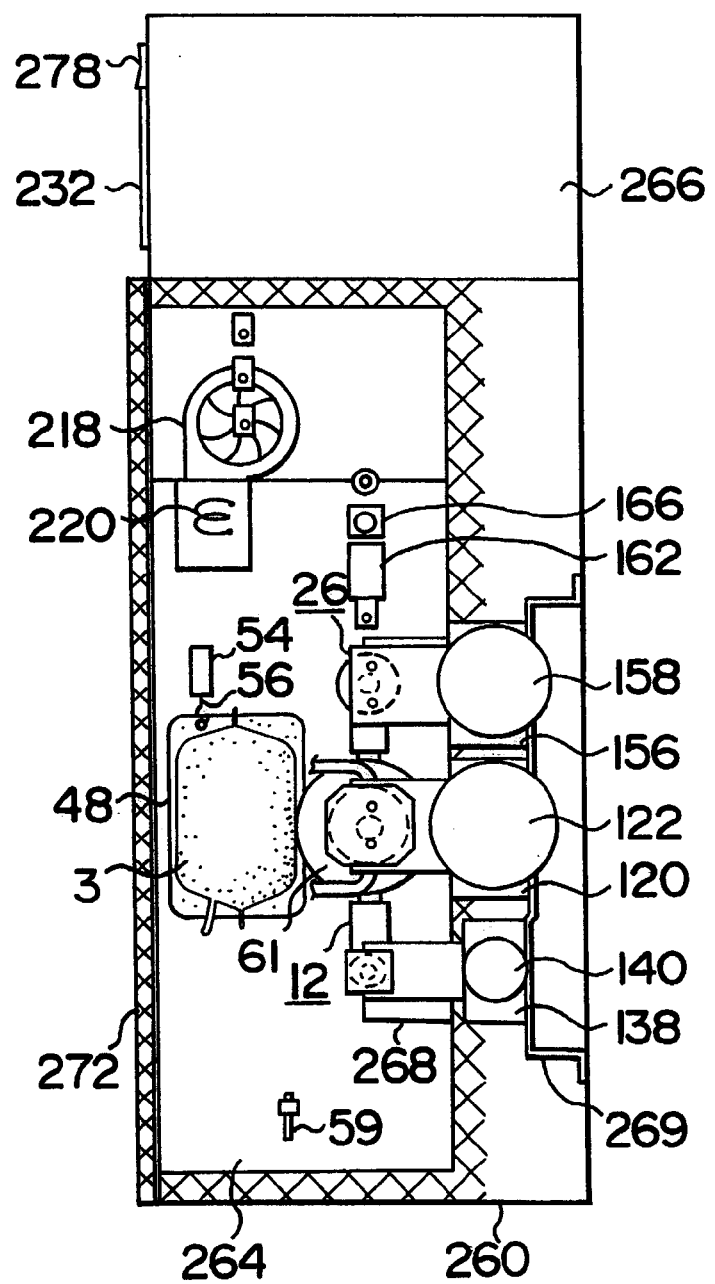
FIG. 15 is a side view of the culture apparatus unit in FIG. 14.
Figure 16:
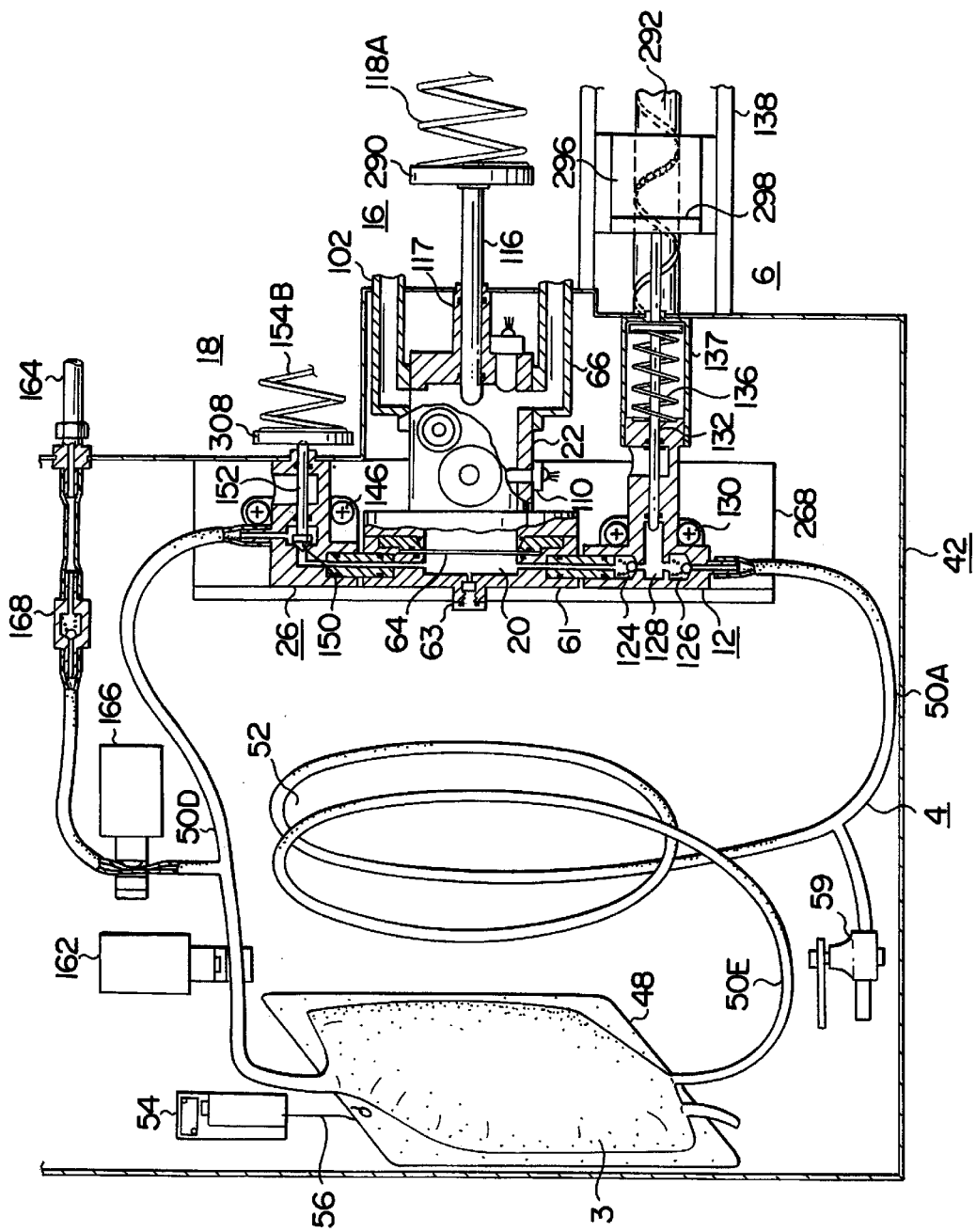
FIG. 16 is a view showing a part of a culture apparatus body and a culture circuit unit in FIG. 14.
Figure 17:
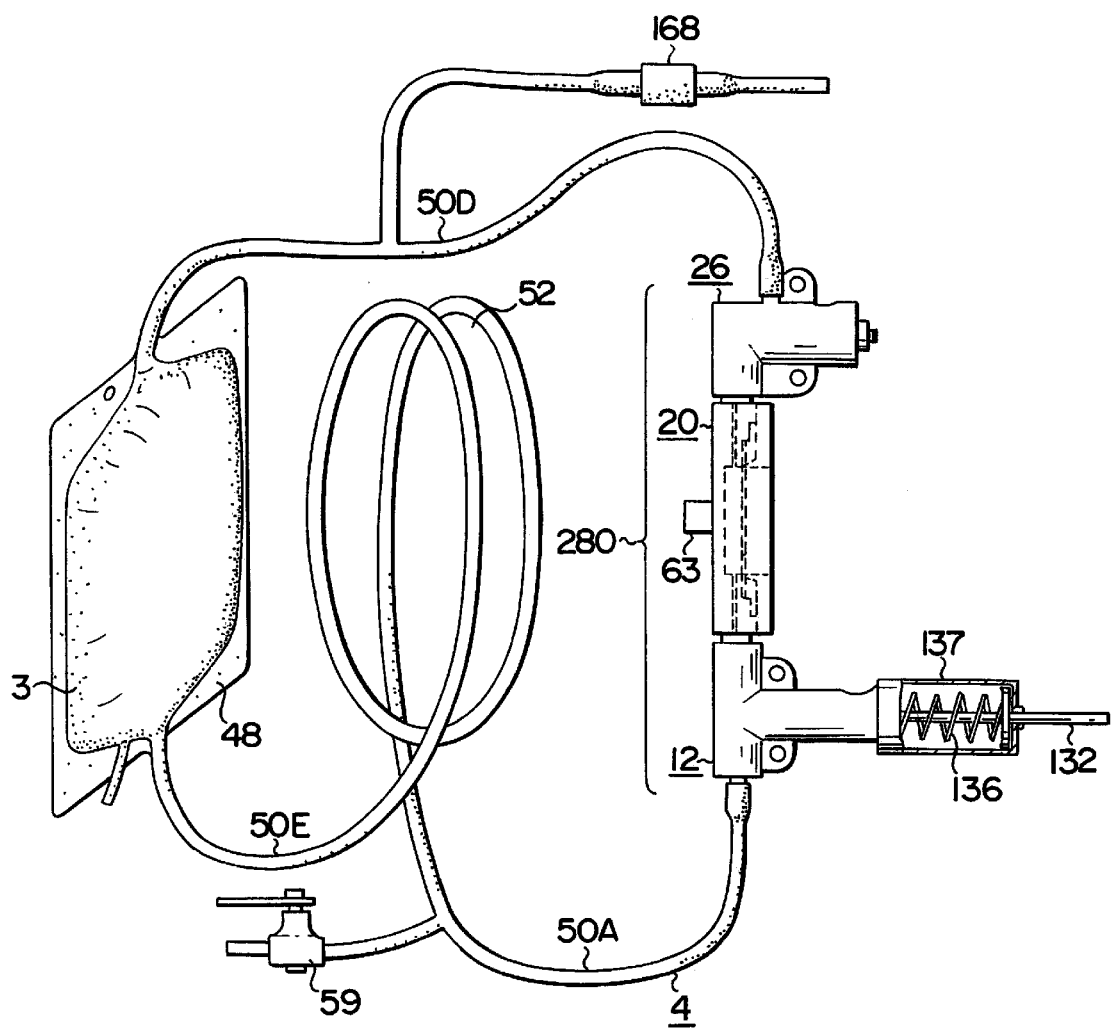
FIG. 17 is a view of the culture circuit unit separated from the culture apparatus body in FIG. 16.
Figure 18:
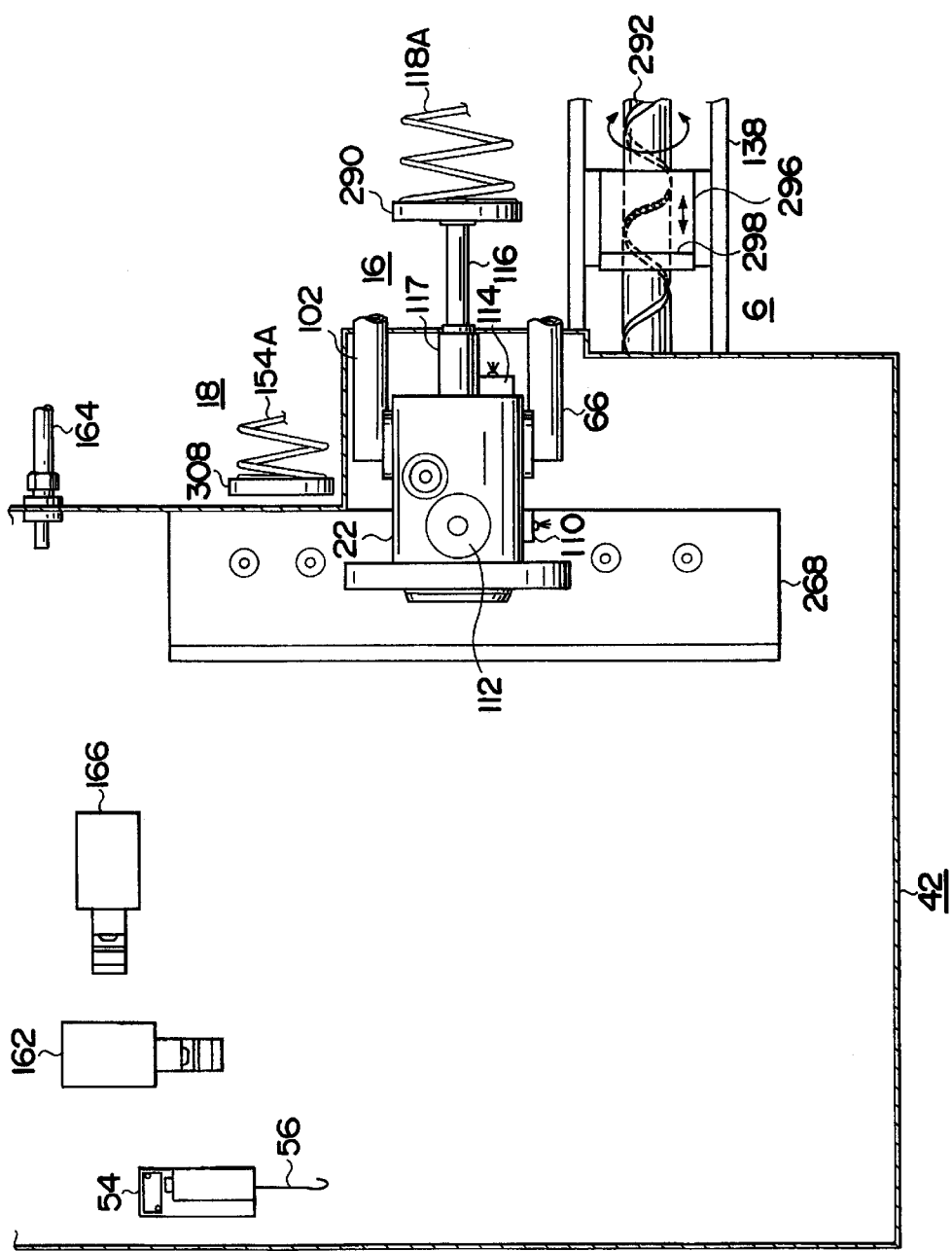
FIG. 18 is a partial sectional view showing a part of the culture apparatus body from which the culture circuit unit in FIG. 16 is removed.
Figure 19:
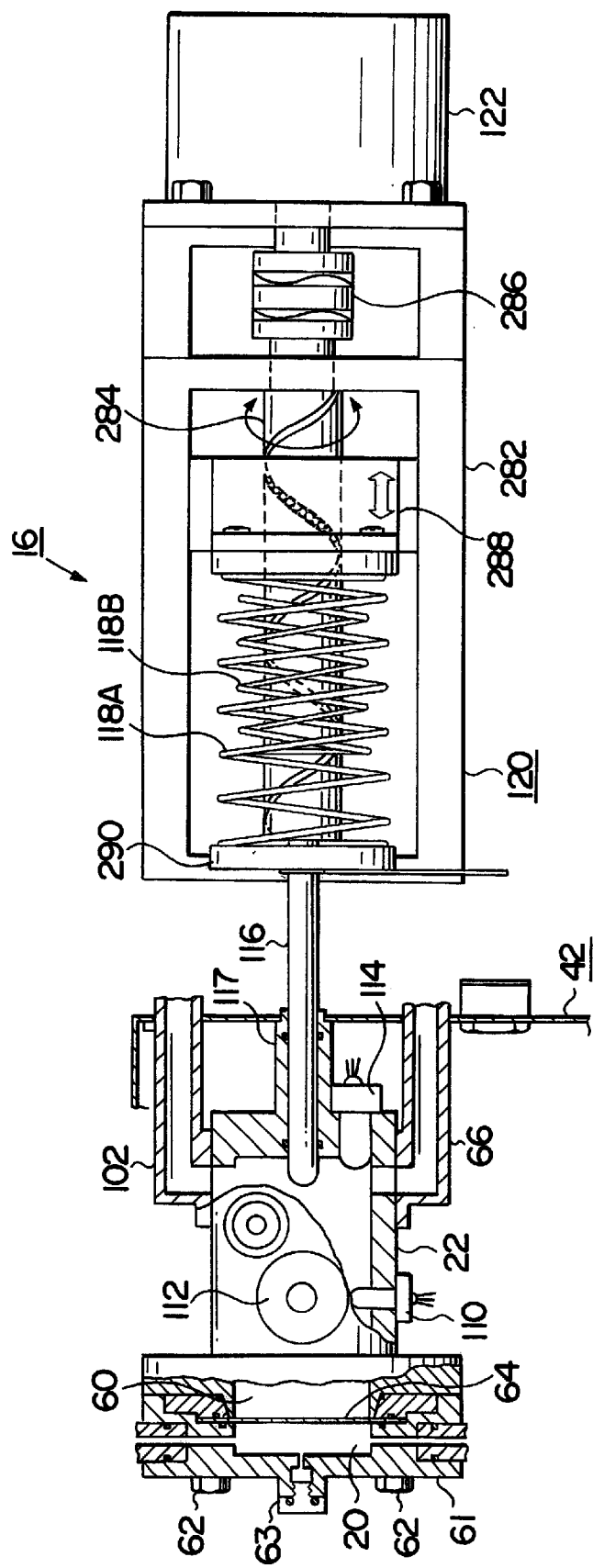
FIG. 19 is a partial sectional view showing a pressure application apparatus of the culture circuit unit in FIG. 16.
Figure 20:
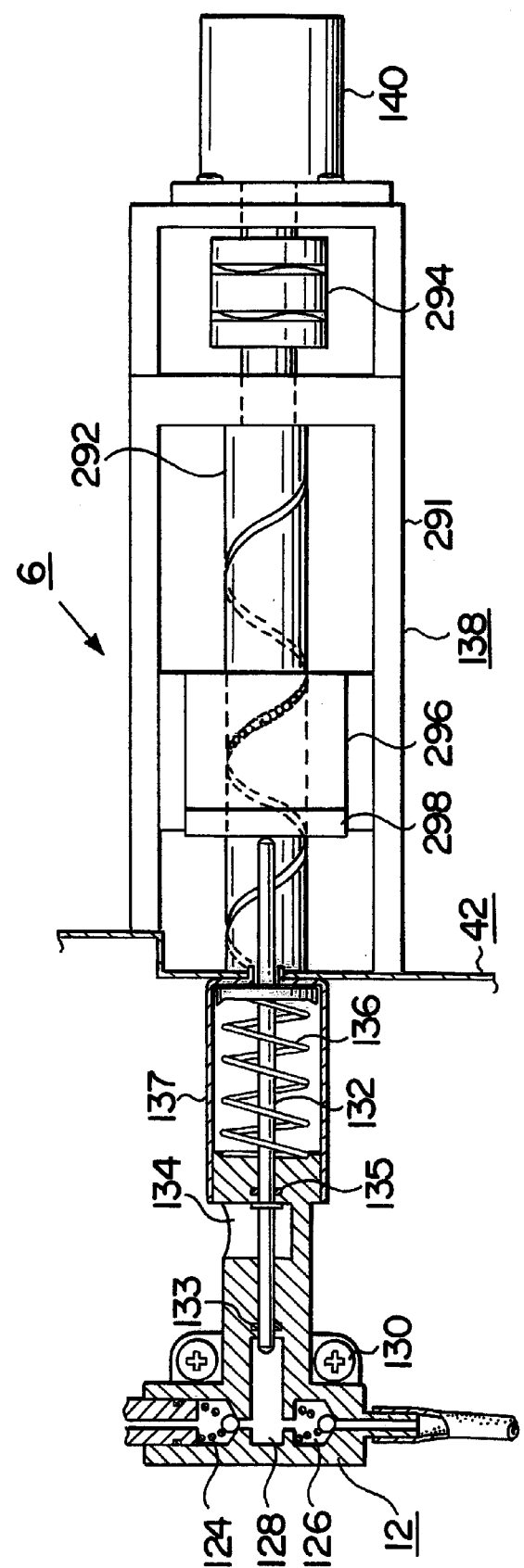
FIG. 20 is a partial sectional view of a culture medium supply apparatus in FIG. 14.
Figure 21:
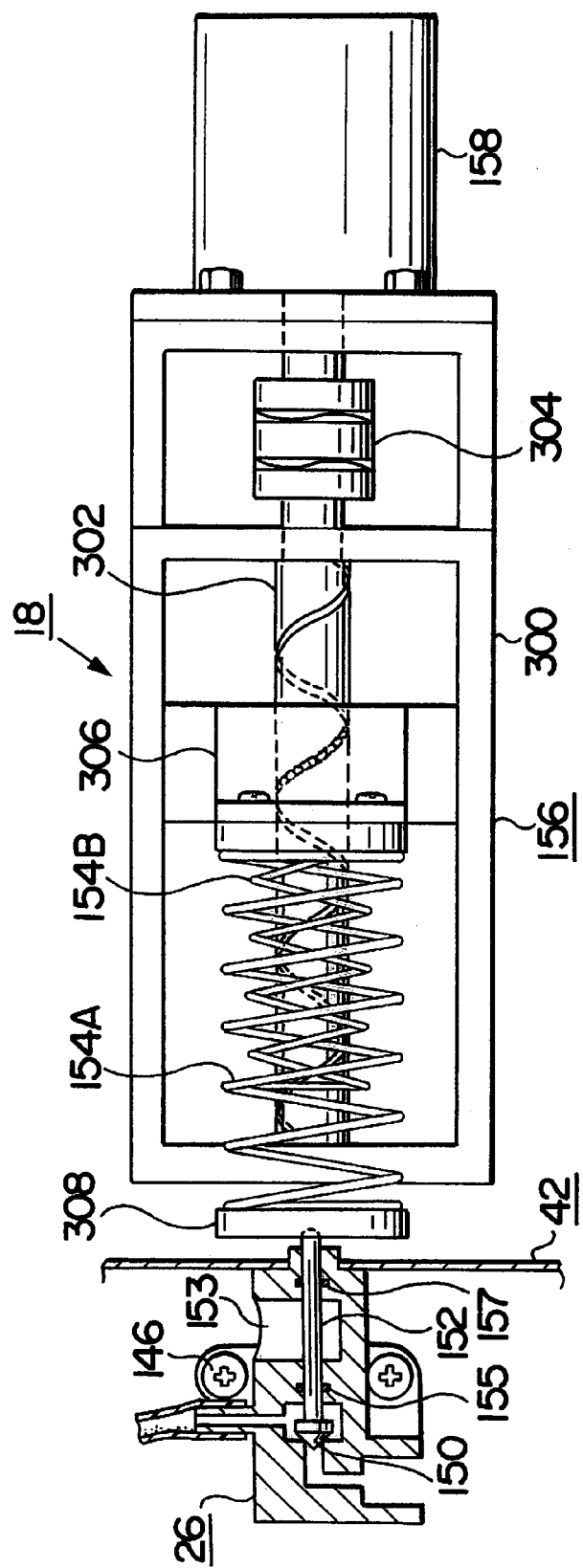
FIG. 21 is a partially sectional view of a pressure buffering apparatus in FIG. 14.

A method of and apparatus for cultivating a cell or tissue according to a second embodiment of the invention is described with reference to FIGS. 14 to 21, wherein FIG. 14 is a front view of the construction of a culture apparatus, FIG. 15 is a side view of the construction of a culture apparatus, FIG. 16 shows a main portion of the culture apparatus, FIG. 17 shows a culture circuit unit 4, FIG. 18 shows a main portion of the culture apparatus excluding the culture circuit unit 4, FIG. 19 shows a pressure application apparatus 16, FIG. 20 shows a culture medium supply apparatus 6, and FIG. 21 shows a pressure buffering apparatus 18. Components which are the same as those in the first embodiment are denoted by the same reference numerals.

The culture apparatus is structured by a single housing 260. The housing 260 is partitioned into a culture chamber 262, a machine chamber 264, and a control/power supply chamber 266. A culture box 42 is accommodated in the culture chamber 262, and it has the same construction as that of the first embodiment except that the culture medium supply apparatus 6, a pressure application apparatus 16, the pressure buffering apparatus 18, and so forth are structure by a single processing portion 268.

Doors 270, 272 which are independently opened or shut are provided respectively in the culture chamber 262 and machine chamber 264. A water tank for pressurizing 68 is accommodated in the machine chamber 264 together with the driving mechanism portions of the culture medium supply apparatus 6, pressure application apparatus 16 and pressure buffering apparatus 18, wherein each of the actuators 120, 138, 156 is supported by the machine chamber 264 at the back side thereof with a common fixing plate 269 as shown in FIG. 15. A water supply port 274 and a water discharge port 276 are respectively provided on a wall surface of the machine chamber 264. A control apparatus 40 and a power supply apparatus are accommodated in the control/power supply chamber 266 and an indication apparatus 232 and a power supply switch 278 are provided on the front panel side of the control/power supply chamber 266.

As shown in FIG. 16, the culture box 42 is accommodated in the culture chamber 262, and the culture circuit unit 4 and the processing portion 268 are accommodated in the culture box 42. A processing unit 280 is detachably provided in the processing portion 268 at the culture circuit unit 4 side as shown in FIGS. 17 and 18.

FIG. 19 shows the pressure application apparatus 16 including a culture vessel 61 and a pressure vessel 22 constituting a culture chamber 20. In this case, an actuator 120 of the pressure application apparatus 16 comprises a housing 282 to which a ball screw 284 is attached, and a motor 122 coupled to the rear end of the ball screw 284 by a coupling joint 286. A movable bed 288 that is moved back and forth by the rotation of the ball screw 284 is provided on the ball screw 284, and two pressure application springs 118A, 118B which are overlapped with each other are provided between the movable bed 288 and a support flange 290 provided at the front end portion of the ball screw 284. That is, the two pressure application springs 118A, 118B are varied in compression state by the movable bed 288 that is moved in response to the rotation of the ball screw 284 so that elasticity of the two pressure application springs 118A, 118B acts on the pressure application piston 116 side. The actuator 120 may be formed of a belt or cam or the like instead of the ball screw 284.

FIG. 20 shows the culture medium supply apparatus 6. The actuator 138 comprises a housing 291 to which a ball screw 292 is attached and a motor 140 is coupled to the rear end portion of the ball screw 292 by a coupling joint 294. A movable bed 296 that is moved back and forth by the rotation of the ball screw 292 is provided on the ball screw 292, and the front surface of a piston pressing board 298 attached to the movable bed 296 contacts the rear end of a medium supply piston 132. That is, when the movable bed 296 that is moved in response to the rotation of the ball screw 292 caused by the motor 140 moves forward to compress the pressure application spring 136, the medium supply piston 132 moves forward so that the movable bed 296 is moved backward. As a result, the compression of the pressure application spring 136 is released and the medium supply piston 132 moves backward by a restoring force of the pressure application spring 136. The culture medium 3 can be supplied when the medium supply piston 132 moves back and forth.

FIG. 21 shows the pressure buffering apparatus 18. In this case, the actuator 156 of the pressure buffering apparatus 18 comprises a housing 300 to which a ball screw 302 is attached, a motor 158 coupled to the rear end portion of the ball screw 302 by a coupling joint 304. A movable bed 306 that is moved back and forth by the rotation of the ball screw 302 is provided on the ball screw 302, and a plunger pressing board 308 is attached to the movable bed 306 by way of buffer springs 154A, 154B which are overlapped with each other, and the rear end of the plunger 152 of a pressure relief valve 26 contacts the front surface of the plunger pressing board 308. That is, when the movable bed 306 that is moved in response to the rotation of the ball screw 302 caused by the motor 158 is moved forward, the plunger pressing board 308 moves forward together with the buffer spring 154A, 154B so that the buffer spring 154A, 154B are varied in compression state. That is, a valve body 150 is pressed by way of the buffer springs 154A, 154B which are in compression state so that the pressure relief valve 26 is held in a blocked state. This holding state is varied in response to the rotation of the ball screw 302 and a compression state of the buffer springs 154A, 154B accompanied by the rotation of the ball screw 302.

Figure 22:
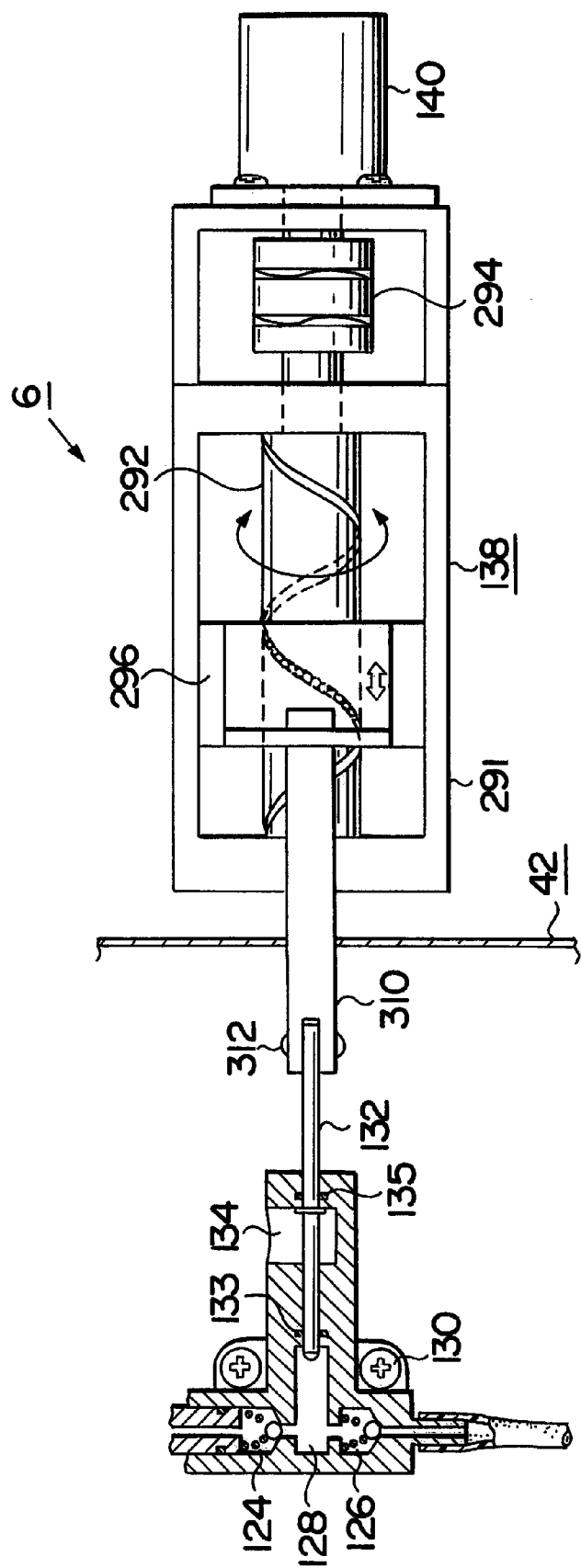
FIG. 22 is a partially sectional view of a culture medium supply apparatus according to a modification of the second embodiment of the invention.

FIG. 22 shows a modification of the culture medium supply apparatus 6. Although the pressure application spring 136 is provided on the medium supply piston 132 in the culture medium supply apparatus 6 shown in FIGS. 2, 3 and 14, it may be possible to attach a connecting shaft 310 to the movable bed 296 that is moved by the ball screw 292 of the actuator 138 while omitting the pressure application spring 136, and the rear end of the medium supply piston 132 is coupled to the tip end of the coupling shaft 310 by way of fixing means such as a fixing pin 312. Even with such a construction, the medium supply piston 132 can be moved back and forth by the normal or reverse rotation of the ball screw 292.

Figure 23:
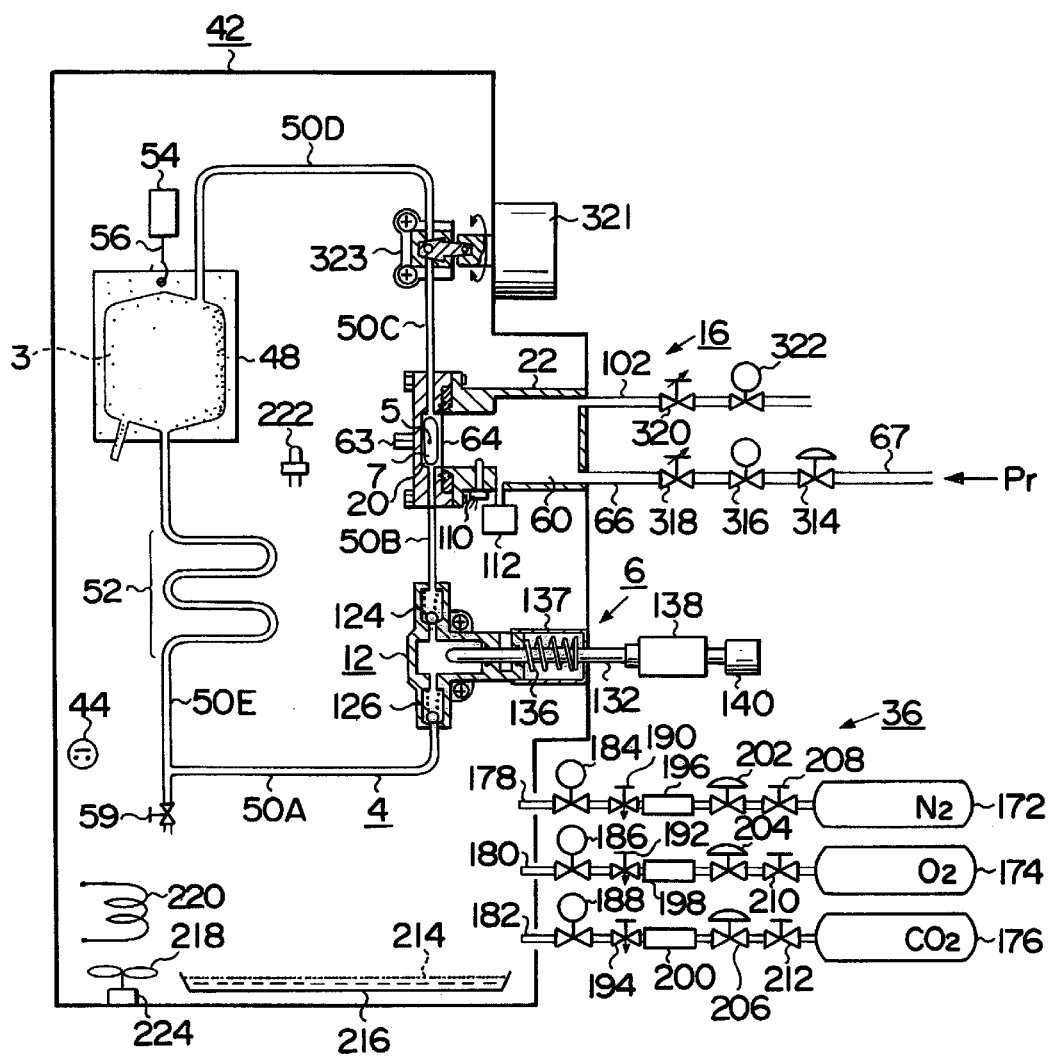
FIG. 23 is a view showing a method of and an apparatus for cultivating a cell or tissue according to a third embodiment of the invention.

Third Embodiment (FIG. 23)

A method of and apparatus for cultivating a cell or tissue according to a third embodiment of the invention is described with reference to FIG. 23. Components which are the same as those in the first and second embodiments are denoted by the same reference numerals.

In the third embodiment, pressurized air from a compressor, not shown is forced to act on the interior of the pressure chamber 60 formed of a pressure vessel 22 of a pressure application apparatus 16 as indicated by an arrow Pr through a conduit 67 on which a pressure regulator 314, a pressure-increasing valve 316 and a needle valve 318 are provided, so that the pressurized air in the pressure chamber 60 is discharged through a collection conduit 102 having a needle valve 320 and a pressure-decreasing valve 322. A valve 323 that is closable by the rotation of an actuator 321 may be provided at the tube 50D side instead of the valve 11 (FIG. 1) or pinch valve 162 (FIG. 2). Pressure application stimulation can be applied to the cell 5 by performing an operation to intermittently block the valve 323 or an operation to apply a pressure to the pressure transmitting film 64 while the pressurized air acts on the pressure transmitting film 64. In this case, the pressure application stimulation can be varied by controlling the pressure-increasing valve 316 and pressure-decreasing valve 322 to be opened and shut. If such pressurized air is employed, the amount of variation in pressure every amount of motion per unit is made small at a low pressure while the amount of variation in pressure every amount of motion per unit is made large at a high pressure, so that unnecessary vibration generated by a motor, an actuator and so forth can be absorbed when a pressure is applied to a cell or tissue, thereby enhancing the accuracy of pressure application stimulation to be applied to the cell or tissue.

Figure 24:
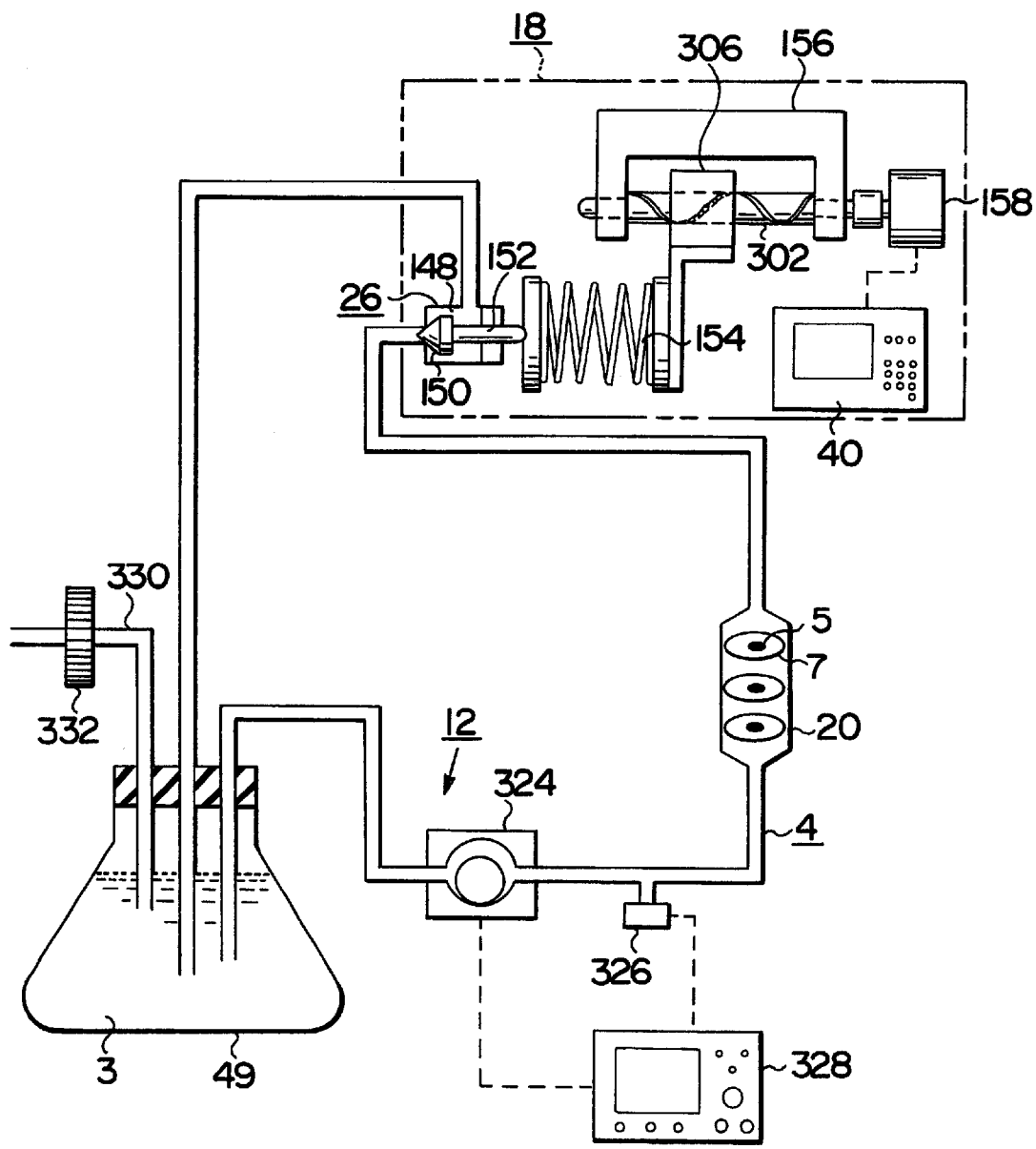
FIG. 24 is a view showing a method of and an apparatus for cultivating a cell or tissue according to a fourth embodiment of the invention.
Figure 25:
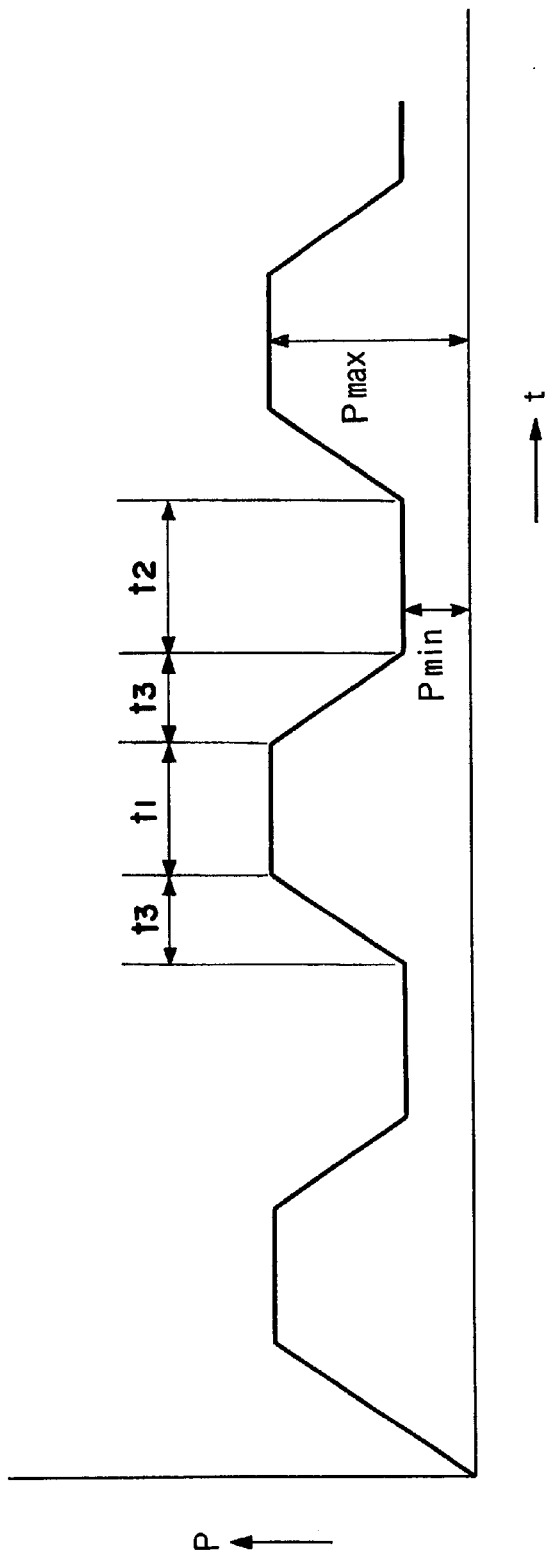
FIG. 25 is a view showing a pressure application operation or control according to a fourth embodiment of the invention.
Figure 26:
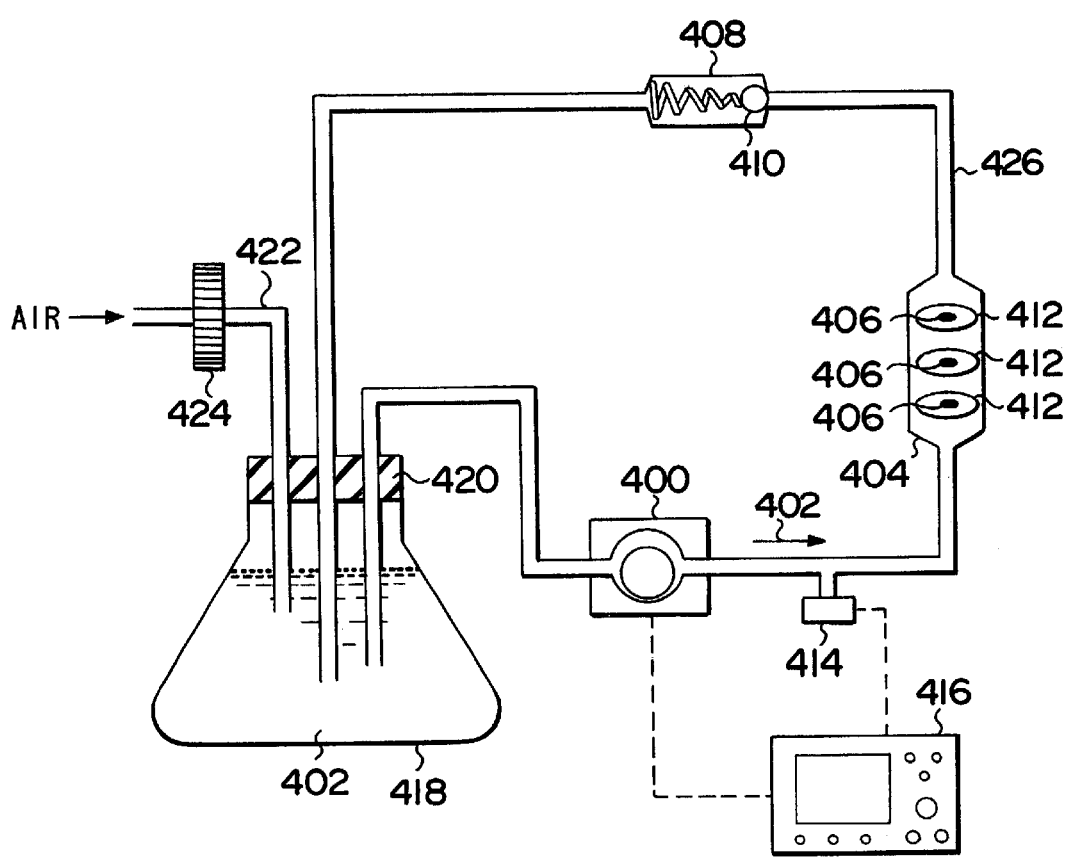
FIG. 26 is a view showing a conventional method of and an apparatus for cultivating a cell or tissue.
Figure 27:
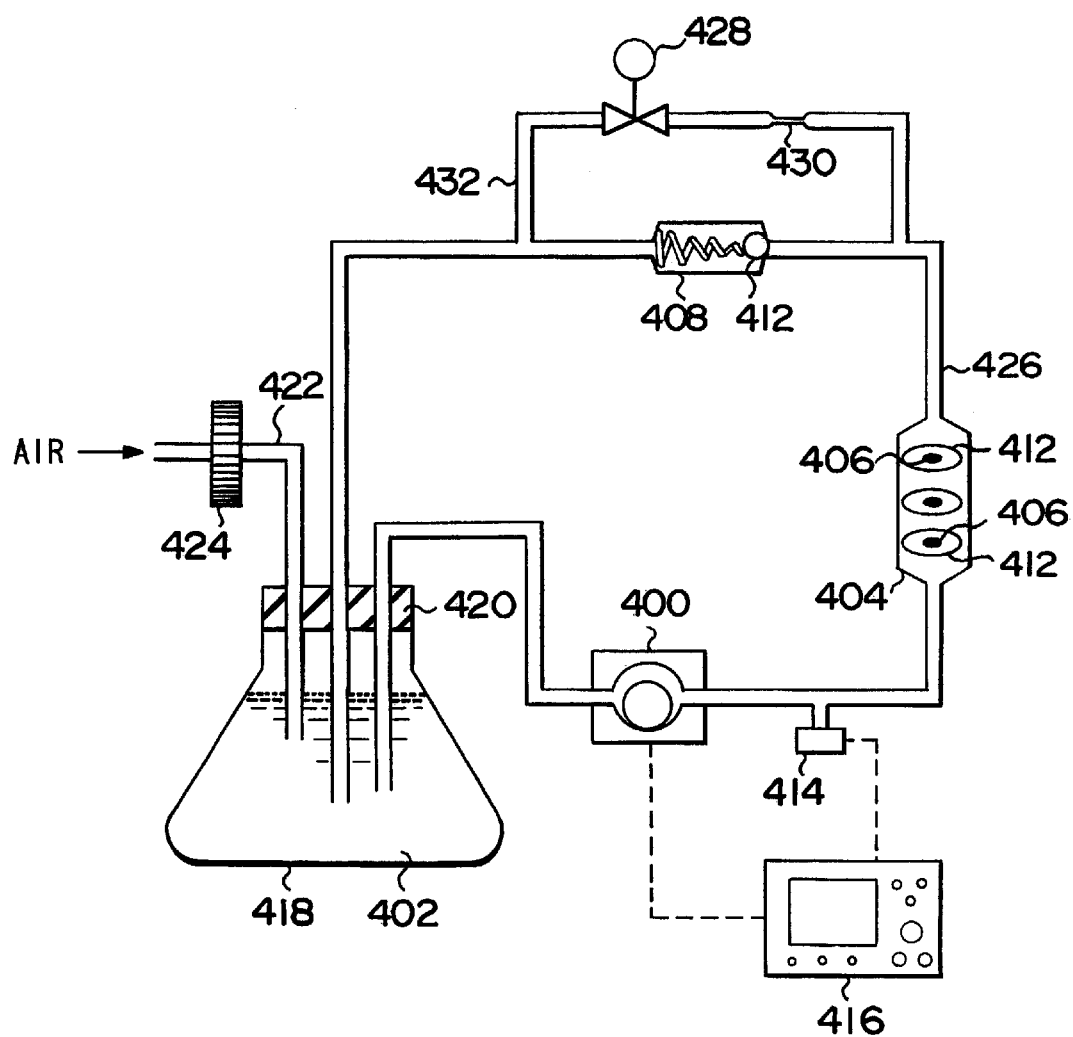
FIG. 27 is a view showing another conventional method of and an apparatus for cultivating a cell or tissue.

Fourth Embodiment (FIGS. 24 and 25)

A method of and apparatus for cultivating a cell or tissue according to a fourth embodiment of the invention is described with reference to FIGS. 24 and 25. Components which are the same as those in the first to third embodiments are denoted by the same reference numerals.

A cell 5 to be cultivated is transplanted in a scaffold 7 formed of a collagen or the like, and it is stored in a culture chamber 20 every scaffold 7. A culture medium 3 is supplied from a culture medium tank 49 to the culture chamber 20 thorough a culture circuit unit 4. The culture circuit unit 4 forms a closed circuit, and a pump 324 serving as the medium supply apparatus 12, a pressure sensor 326 and a pressure buffering apparatus 18 are provided on the culture circuit unit 4. A pressure detected by the pressure sensor 326 is applied to a pressure controller 328, and a control output corresponding to the detected pressure is applied to the pump 324 from the pressure controller 328. That is, a pressure P of the culture medium 3 is controlled to have a fixed value.

The pressure buffering apparatus 18 comprises an actuator 156 attached to a plunger 152 of a valve body 150 of a pressure relief valve 26 which is inserted into a part of the culture circuit unit 4 by way of a buffer spring 154, and a motor 158 coupled to the actuator 156. The rotation of the motor 158, namely, a normal rotation, a reverse rotation, a stop of rotation and an rpm are controlled by a control apparatus 40. That is, the rotation of the motor 158 is transmitted to a ball screw 302, and a movable bed 306 is moved back and forth in response to the direction of rotation of the ball screw 302. Since a motion of the movable bed 306 is transmitted to the plunger 152 of the valve body 150 by way of the buffer spring 154, a force to shut the valve body 150 is set by a position of the movable bed 306 and a compression force of the buffer spring 154. When a pressure of the culture medium 3 caused by the pump 324 exceeds a force to shut the valve body 150, the valve body 150 is opened so that the culture medium 3 passes through the pressure relief valve 26.

An air conduit 330 through which a gas such as oxygen or carbon dioxide is taken is provided in the culture medium tank 49, and a filter 332 for preventing the entrance of bacteria, a foreign matter and so forth is provided on the air conduit 330. That is, oxygen or carbon dioxide that is taken in the culture medium tank 49 through the air conduit 330 is transmitted to the cell 5 inside the culture chamber 20 together with the culture medium 3.

With such a construction, when the pump 324 is driven, the culture medium 3 is supplied to the culture circuit unit 4 and flows in the culture chamber 20 so as to supply nutrition and a gas such as oxygen or carbon dioxide that are needed for the cell 5. When the pressure buffering apparatus 18 is driven, the culture circuit unit 4 is blocked so that a pressure inside the culture chamber 20 is increased by a pressure applied from the pump 324 to the culture medium 3. A buffering force of the pressure buffering apparatus 18, namely, an arbitrary pressure value that is balanced with a pressure applied from the pump 324 can be obtained by controlling a force for shutting the valve body 150.

FIG. 25 shows a pressure application operation. When the pressure buffering apparatus 18 is operated periodically, the maximum pressure Pmax and the minimum pressure Pmin can be alternately applied to the cell 5. That is, in the cell 5, the maximum pressure Pmax is set for time $t_1$, the minimum pressure Pmin is set for time $t_2$, and also pressure-increase time $t_3$ and pressure-decrease time $t_3$ are set so that the circulation of the culture medium 3 under pressure is achieved like a living body and a growth environment is achieved like the living body. When an operation speed of the pressure buffering apparatus 18 is controlled, time $t_1$, $t_2$, $t_3$ can be arbitrarily controlled, thereby achieving an optimal state corresponding to the characteristic of the cell 5 to be cultivated or the living body at a specific position. The method of and apparatus for cultivating a cell or tissue according to the invention can obtain the following effects.

a. It is possible to cultivate a cell or tissue under an environment mimicking the living body without being contaminated, and possible to cultivate the cell or tissue which is close to a tissue in a living body and easily fusible with a tissue in a living body.

b. It is possible to realize the culture of a cell or tissue which is ideal and practical, corresponding to specific position of a living body to be restored, namely, close to a tissue in a living body and is easily fusible with a tissue in a living body by holding a cell or tissue of a living body at a specific culture position, setting the cell or tissue under an environment mimicking the living body, supplying continuously or intermittently a culture medium to the cell or tissue, and applying a pressure which is varied continuously, a pressure which is varied intermittently or a pressure which is varied periodically to the cell or tissue.

c. It is possible to cultivate a cell or tissue efficiently in a extremely stabilized state by holding a cell or tissue to be cultivated in a suspending or non-suspending state in the culture medium.

d. It is possible to enhance the culture of a cell or tissue by holding a cell or tissue in a suspending state in the culture medium by a hydro-gel or a scaffold.

e. It is possible to perform an efficient culture or cultivate the cell or tissue having high quality because the culture medium comprises one of amino acids of various types, saccharides, salts and protein, or not less than two of materials selected therefrom or all of these materials.

f. It is possible to cultivate a cell or tissue which is easily fusible with a tissue in a living body because physiological conditions of the living body at a specific position, an age, a height, a weight, a sex of the living body and other information inherent in the living body in addition to the physiological conditions.

g. It is possible to realize the control of an environment close to a living body, and possible to contribute to the culture of a cell or tissue which is close to a tissue in a living body and is easily fusible with a tissue in the living body because a living body environment is set by supplying and controlling a nitrogen gas, an oxygen gas, a carbon dioxide gas and by setting and controlling a temperature and a humidity.

h. It is possible to form a cell or tissue which is ideal and practical by applying a pressure to the cell or tissue, corresponding to a living body at a specific position to be restored.

i. It is possible to realize ideal physical stimulation by selecting or combining modes of a pressure pattern which is varied continuously, intermittently or periodically, which affects metabolism function, cell division cycle, concentration gradient or dispersion of living body stimulation, thereby enhancing the culture.

j. It is possible to protect or prevent a cell or tissue which is intercepted from an open air from being contaminated by bacteria to cultivate a high quality cell because a culture unit allows a cell or tissue to be cultivated to be accommodated in a culture chamber and supplies culture medium needed for the cell or tissue which is intercepted from an open air. Further, a desired pressure by pressure application means as well as a hydraulic pressure by culture medium and physical stimulation by flow of culture medium are applied to a cell or tissue, the cell or tissue susceptible to metabolism function, cell division cycle, concentration gradient or dispersion of living body stimulation, thereby enhancing culture of the cell or tissue. Still further, since the mode of supply of culture medium to a cell or tissue is arbitrarily set by culture medium supply means so that culture medium can be supplied intermittently or continuously, thereby enhancing culture by a variety of physical stimulation.

k. It is possible to mimic the living body, set a desired environment, and perform an efficient culture by arbitrarily controlling the pressure application means or culture medium supply means using control means, and performing various program controls such as a feed back control or feed forward control by the control means such as a computer.

l. The manner of applying a pressure, namely, a pressure pattern is set in response to the cell or tissue to be cultivated, thereby performing more efficient culture.

m. It is possible to perform efficient culture by setting a pressure pattern in all modes, and selecting or combining thereof.

n. It is possible to protect or prevent the cell or tissue from being contaminated by bacteria and so forth during the motion thereof to enhance a reliability such as restoration of a living body because the culture unit having a culture chamber for accommodating the cultivated cell or tissue is independent of and detachable from a culture apparatus body, so as to move the cell or tissue together with the culture unit that is separated from an open air.

o. It is possible to set a culture environment by the supply of a desired gas because a hermetically sealed space serving as a culture space is intercepted from an open air, and also protect or prevent the cell or tissue from being contaminated by the open air.

p. It is possible to apply a gas to the cell or tissue by supplying a gas such as a nitrogen gas, an oxygen gas, a carbon dioxide gas and providing gas absorption means in a culture unit and possible to mimic a living body environment by supplying and controlling the gas.

q. It is possible to mimic a living body environment and provide a desired culture space by filling a nitrogen gas, an oxygen gas, a carbon dioxide gas into the culture space formed by a hermetically sealed space.

r. It is possible to prevent culture medium from being contaminated by providing a culture medium tank for supplying the culture medium to the culture unit or circulating the culture medium and installing it in a hermetically sealed space that is intercepted from the open air.

s. It is possible to apply pressure application stimulation to a cell or tissue accommodated in a culture chamber in a state wherein it is intercepted from an open air, and to realize desired pressure application stimulation such as stimulation mimicking a living body environment by providing a pressure transmitting film.

t. It is possible to realize physical stimulation close to a living body environment and to enhance the culture of a cell or tissue by regulating a pressure by pressure buffering means when a part of a culture unit is pressurized.

u. It is possible to realize desired pressure application stimulation and to mimic a living body environment with high accuracy by using either of a hydraulic pressure, an oil pressure or an air pressure as pressure forming means.

v. It is possible to supply and circulate a culture medium efficiently to a culture unit if the culture medium means comprises a medium supply apparatus for pressuring the culture medium that is taken in the medium supply chamber and possible to set the amount of desired supply of medium by controlling the amount of applied pressure.

w. It is possible to apply ideal pressure application stimulation to the cell or tissue because a pressure to be applied to the culture medium is buffered, and possible to control the culture medium in an ideal pressure state, when using the pressure relief valve, without contaminating the culture medium if the pressure of the culture medium is decreased by opening the pressure relief valve while controlling the pressure relief valve.

x. It is possible to provide a culture space conforming to a living body environment by controlling a temperature and a humidity of a hermetically sealed space in which the culture unit is accommodated.

y. It is possible to mimic a living body environment acoustically by using a sound producing unit together because a living body receives acoustic stimulation from the outside, and possible to inject the cell or tissue to be cultivated in a culture chamber by use of a super-sound wave together with high reliability.

z. It is possible to mimic a living body environment to contribute to the enhancement of culture of a cell or tissue by controlling the concentration of a gas to be supplied to a hermetically sealed space by controlling means.

Although the construction, function and effect of the method of and apparatus for cultivating a cell or tissue according to the first to fourth embodiments of the invention are described, the invention is not limited to these embodiments, and the invention includes all constructions such as various constructions, modifications, and so forth which can be expected or conjectured based on the object and the embodiments of the invention.

What is claimed is:

1. A method of cultivating a cell or tissue comprising the steps of:

providing a sealed space into which a gas is supplied, wherein the space is maintained at a temperature and environment necessary for sustaining life;

installing a culture medium bath and a culture chamber inside the sealed space, and forming a culture circuit by connecting the culture medium bath and the culture chamber by a tube, wherein the culture medium is circulated from the culture medium bath to the culture chamber through the culture circuit;

circulating the culture medium in the culture circuit by providing a continuous supply, intermittent supply, periodic supply, or a combination thereof of the culture medium to the culture circuit;

providing means for holding the cell or tissue in a suspending or non-suspending state in the culture medium within the culture chamber;

allowing the gas in the sealed space to permeate through a gas absorption portion separately provided at a part of the culture circuit at a front stage of the culture chamber, wherein the gas is absorbed in the culture medium in front of the culture chamber; and applying a pressure to the cell or tissue held in the culture medium within the culture chamber to cultivate the cell or tissue, wherein the pressure applied to the cell or tissue is fixed continuous pressure, continually varying pressure, periodic changes in pressure, or a combination thereof.

2. A method of cultivating a cell or tissue according to claim 1, wherein the pressure applied to the cell or tissue to be cultivated is set in according to pressures found in a living body corresponding to the cell or tissue to be cultivated.

3. A method of cultivating a cell or tissue according to claim 1, wherein the sealed space is maintained at humidity conditions necessary for sustaining life.

* * * * *